(12) United States Patent
Lee et al.

(10) Patent No.: US 7,741,618 B2
(45) Date of Patent: Jun. 22, 2010

(54) ENHANCED PORTABLE DIGITAL LIDAR SYSTEM

(75) Inventors: Hyo Sang Lee, Silver Spring, MD (US); In Heon Hwang, Columbia, MD (US); Coorg R. Prasad, Silver Spring, MD (US)

(73) Assignee: Science & Engineering Services, Inc., Columbia, MD (US)

( * ) Notice: Subject to any disclaimer, the term of this patent is extended or adjusted under 35 U.S.C. 154(b) by 1098 days.

(21) Appl. No.: 11/281,621

(22) Filed: Nov. 18, 2005

(65) Prior Publication Data

US 2006/0231771 A1    Oct. 19, 2006

Related U.S. Application Data

(60) Provisional application No. 60/628,925, filed on Nov. 19, 2004.

(51) Int. Cl.
*G01J 1/58* (2006.01)

(52) U.S. Cl. .................................................. 250/458.1

(58) Field of Classification Search ............... 250/458.1
See application file for complete search history.

(56) References Cited

U.S. PATENT DOCUMENTS

| | | | |
|---|---|---|---|
| 2,790,081 A | 4/1957 | Munday | |
| 3,858,046 A | 12/1974 | Cubalchini | |
| 4,663,961 A | 5/1987 | Nelson et al. | |
| 4,812,025 A * | 3/1989 | Miller | ...................... 359/712 |
| 5,202,570 A | 4/1993 | Tanaka et al. | |
| 5,216,484 A | 6/1993 | Chao et al. | |
| 5,373,160 A | 12/1994 | Taylor | |
| 5,793,049 A | 8/1998 | Ballard | |
| 6,593,582 B2 | 7/2003 | Lee et al. | |
| 6,876,790 B2 | 4/2005 | Lee | |
| 2003/0030001 A1 | 2/2003 | Cooper et al. | |

OTHER PUBLICATIONS

U.S. Appl. No. 11/104,505, filed Apr. 13, 2005, Lee et al.

* cited by examiner

*Primary Examiner*—David P Porta
*Assistant Examiner*—Marcus H Taningco
(74) *Attorney, Agent, or Firm*—Oblon, Spivak, McClelland, Maier & Neustadt, L.L.P.

(57) ABSTRACT

A system for detecting airborne agents. The system can include a laser source that provides laser pulses of at least two wavelengths, a transmitter that transmits the laser pulses, and a coupling mechanism configured to remotely couple the laser pulses between the laser source and the transmitter. The system can include a receiver receives both elastically backscattered signals from airborne agents and fluorescence signals from the airborne agents. The system can include a telescope both transmits a collimated laser beam of the laser pulse from the transmitter to a far field and receives the elastically backscattered signals and the fluorescence signals from the far field. The system can include a detection system having at least one of a backscatter optical detector that detects the elastically backscattered signals and one or more fluorescence optical detectors that detect the fluorescence signals in selected spectral band(s) from the airborne agents.

95 Claims, 15 Drawing Sheets

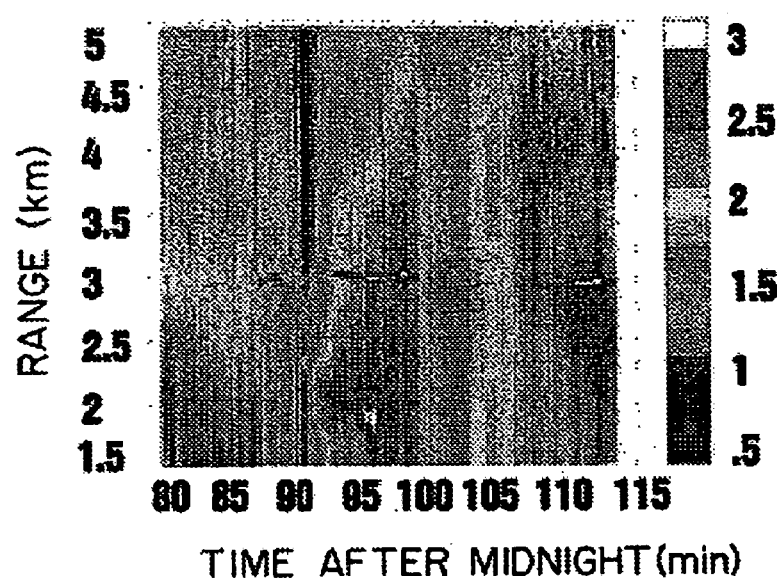
F I G. 2A
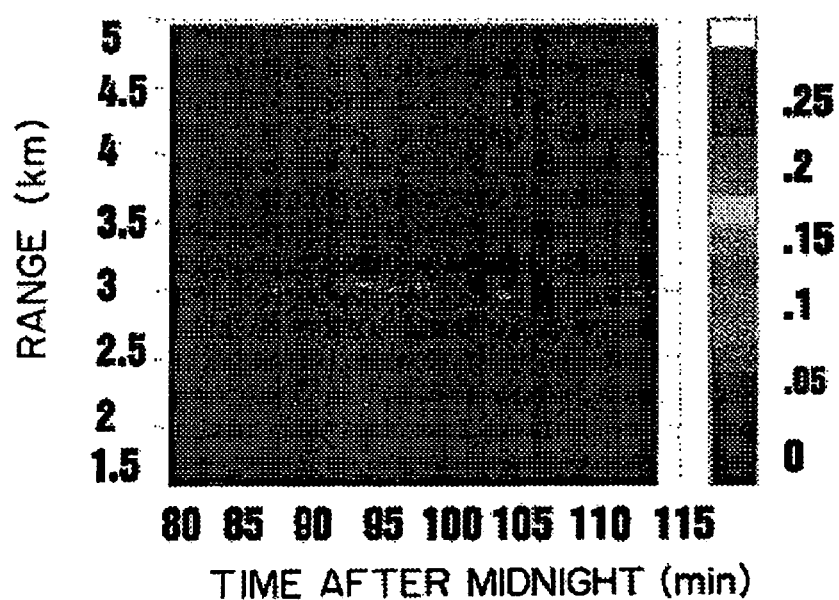
F I G. 2B

US 7,741,618 B2

ENHANCED PORTABLE DIGITAL LIDAR SYSTEM

CROSS REFERENCE TO RELATED APPLICATIONS

This application is related to U.S. patent application Ser. No. 09/852,782 entitled "Portable Digital Lidar (PDL)", filed on May 11, 2001, now U.S. Pat. No. 6,593,582 B2, the entire contents of which are incorporated herein by reference. This application is related to U.S. patent application Ser. No. 10/146,920 entitled "A Method of Coupling a Laser Signal to an Optical Carrier", filed on May 17, 2002, the entire contents of which are incorporated herein by reference now published as U.S. Pat. Application Publication No. US 2003/0215181 A1. This application is related to and claims priority under 35 U.S.C. §119(e) to U.S. Ser. No. 60/628,925, the entire contents of which are incorporated herein by reference.

BACKGROUND OF THE INVENTION

1. Field of the Invention

The present invention relates to a portable light detecting and ranging (LIDAR) system used, for example a for long-range detection of biological weapon (biological warfare agent) aerosol clouds. As such, the present invention can provide early warning for field personnel, providing time for personnel to prepare for the arriving aerosol clouds.

2. Discussion of the Background

Remote stand-off detection of chemical/biological (chem/bio) agents is considered to be a critical necessity in early warning systems enabling maximum survivability of personnel in the battlefield and other sensitive areas. Pulsed elastic backscatter lidar operating in the visible, as described by Lee, et al, "Micro Pulse Lidar for Aerosol & Cloud Measurement", Advances in Atmospheric Remote Sensing with Lidar, pp 7-10, A. Ansmann, Ed., Springer Verlag, Berlin, 1997, the entire contents of which are incorporated herein by reference, and near IR, as described by Condatore, et al, "U.S. Army Soldier and Biological Chemical Command Counter Proliferation Long Range—Biological Standoff Detection System (CP LR BSDS)", Proceedings of SPIE, Vol. 3707, 1999, the entire contents of which are incorporated herein by reference, have demonstrated the high sensitivity and long-range (up to 50 km) capability to detect aerosol clouds. Consequently, aerosol lidar is a chosen technique for long-range detection of bio-warfare aerosols. However, single wavelength aerosol lidars, as currently employed, do not provide discrimination between biological weapon (BW) agent aerosols and other natural or interferent aerosol clouds. The capability to differentiate can be augmented by using multiple wavelength and/or multiple polarization elastic scattering signatures. However, the elastic scattering technique lacks the required specificity for deterministic application of the data in the battle field.

Aerosol lidar is an ideal complement to uv fluorescence lidar, as demonstrated by Wilson, et al, "Development of IR and UV Lidar systems for standoff detection of airborne biological materials" Final Report, Contract DAAA15-91-C-0138, STC Technical Report, 1993, the entire contents of which are incorporated herein by reference, which discloses a UV laser that excites fluorescence from the biological constituents of the aerosol and measures the fluorescence signature of the biological constituents to provide specificity for discrimination between bio-aerosols and other naturally occurring or interfering aerosols. Since atmospheric absorption at UV wavelengths is high and fluorescence cross-section of the target particles is small, even the use of a high energy laser source with a large aperture telescope only enables conventional fluorescence lidar to achieve a range coverage of three to four kilometers. Jezek and Cannaliato, "Biological Standoff Detection", Joint Workshop on Standoff Detection for Chemical and Biological defense, pp. 26-30, October 1998, the entire contents of which are incorporated herein by reference, have been actively developing both long range and short range sensor systems. Long-range biological standoff detection system LR BSDS, as described in Condatore, et al, "U.S. Army Soldier and Biological Chemical Command Counter Proliferation Long Range—Biological Standoff Detection System (CP LR BSDS)", Proceedings of SPIE, Vol. 3707, 1999, the entire contents of which are incorporated herein by reference, is based on elastic scatter aerosol lidar. Short range biological standoff detection system SR BSDS, as described in Suliga, et al, "Short Range Biological Standoff Detection System (SR-BSDS)", Fourth Joint Workshop on Standoff Detection for Chemical and Biological Defense, Sep. 15, 1998, the entire contents of which are incorporated herein by reference, is based on fluorescence and aerosol lidar.

Current chem/bio defense detection systems can provide a rapid indication of a possible BW attack by utilizing multiple independent technologies to provide separate lines of data, which are less likely to be wrong at the same time, thus reducing false alarms. However, present technologies, owing to the complexity and laser power levels required for fluorescence and aerosol lidar, are limited in range and not well suited for an in-the-field, portable early warning detection system.

SUMMARY OF THE INVENTION

For an aerosol stand-off detection sensor to be suitable for civilian and military applications, the sensor is preferably easy to set up in the field, eye-safe, operates autonomously to detect, track and discriminate bio-aerosol clouds, and is modular to allow easy maintenance.

Accordingly, one object of the present invention is to provide an early warning detection system which can provide accurate detection of biological weapons at sufficient distance to provide an adequate response time.

Another object of the present invention is to integrate multiple analysis techniques into a detection system to reduce the probability of false alarms.

Still a further object is to provide a self-aligned detection system which improves reliability of the detection system in the field.

A further object of the present invention is to provide a digital detection system which can by multiplexing improve the signal-to-noise ratios and the detected signals.

Various of these and other objects are achieved in a system for detecting airborne agents. The system can include a laser source that provides laser pulses of at least two wavelengths, a transmitter that transmits the laser pulses, and a coupling mechanism configured to remotely couple the laser pulses between the laser source and the transmitter. The system can include a receiver receives both elastically backscattered signals from airborne agents and fluorescence signals from the airborne agents. The system can include a telescope that both transmits a collimated laser beam of the laser pulse from the transmitter to a far field and receives the elastically backscattered signals and the fluorescence signals from the far field. The system can include a detection system having at least one of a backscatter optical detector that detects the elastically backscattered signals and one or more fluorescence optical detectors that detect the fluorescence signals in selected spectral band(s) from the airborne agents.

In one aspect of the present invention, the system includes separate modules, for example one for the laser source and one for the transmitter/receiver. Coupling between the separate modules is accomplished in one aspect of the invention by a special detachable fiber optic system (i.e., a coupling mechanism) by which high power laser output can be transmitted from the laser to the lidar transmitter, thus permitting the laser and the lidar transmitter to be placed in separate modules. This feature facilitates maintenance and servicing of the laser and transportation.

It is to be understood that both the foregoing general description of the invention and the following detailed description are exemplary, but are not restrictive of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2A-2B are false color plots showing aerosol backscatter time-series data for both the visible and near-IR wavelengths;

FIG. 4C is a flow chart illustrating one computer-implemented method according to an embodiment of the present invention for analyzing the digital lidar signature;

DESCRIPTION OF PREFERRED EMBODIMENTS

Figure 1:
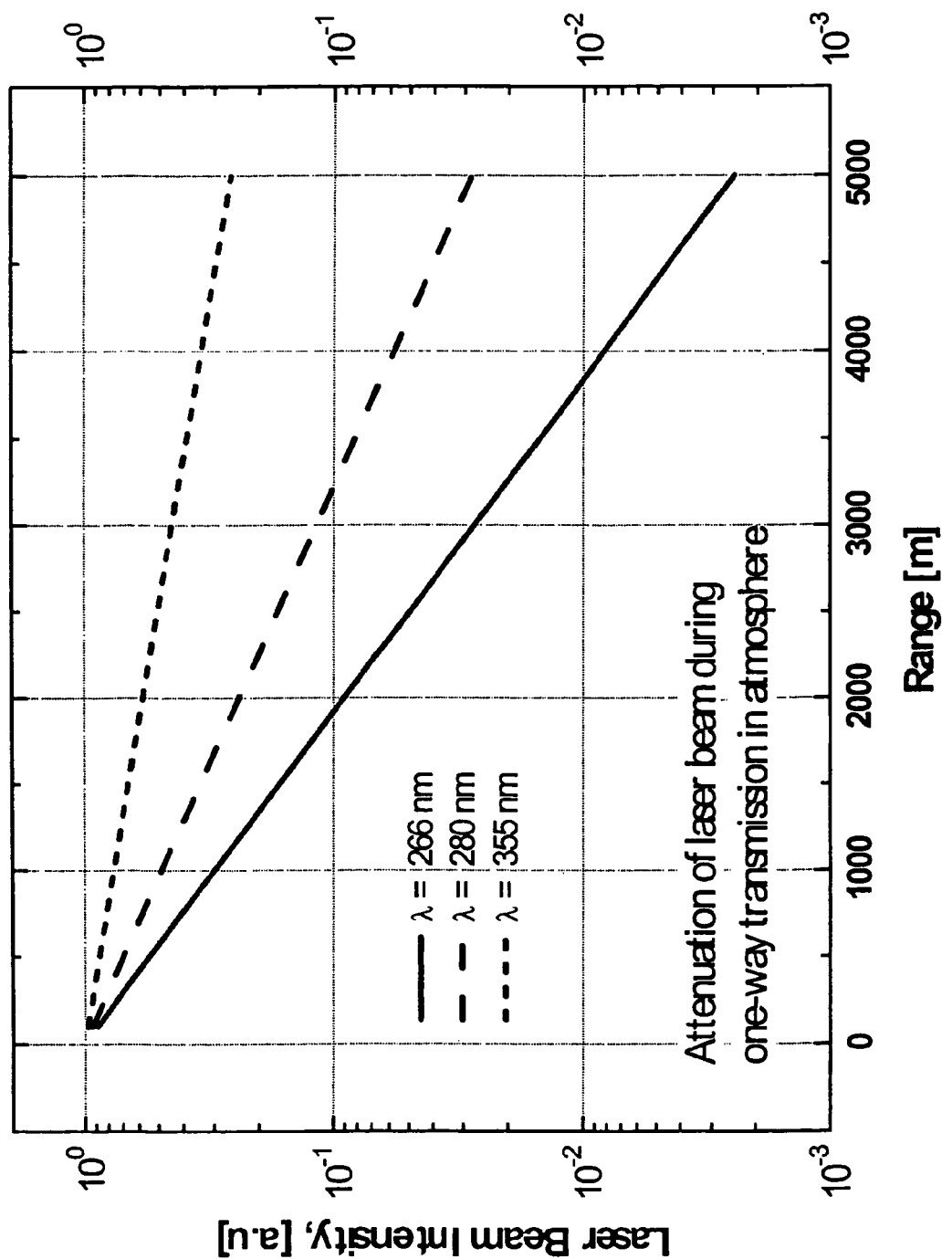
FIG. 1 is a diagram showing at the three wavelengths (266, 280 and 355 nm) the reduction in the laser beam intensity due to scattering and absorption by atmospheric constituents as the laser beam travels to a target.
Figure 2C:
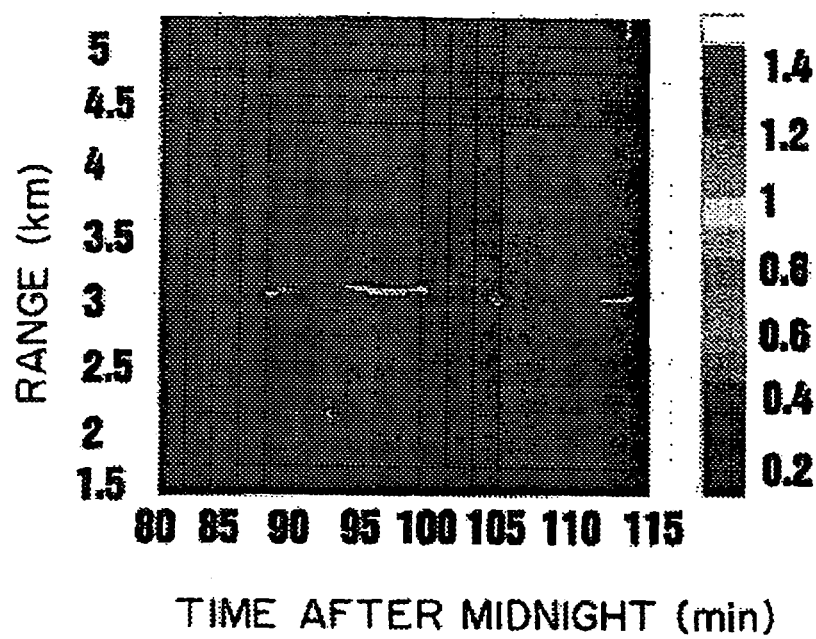
FIG. 2C-2D are false color plots showing fluorescent lidar signal data.
Figure 2D:
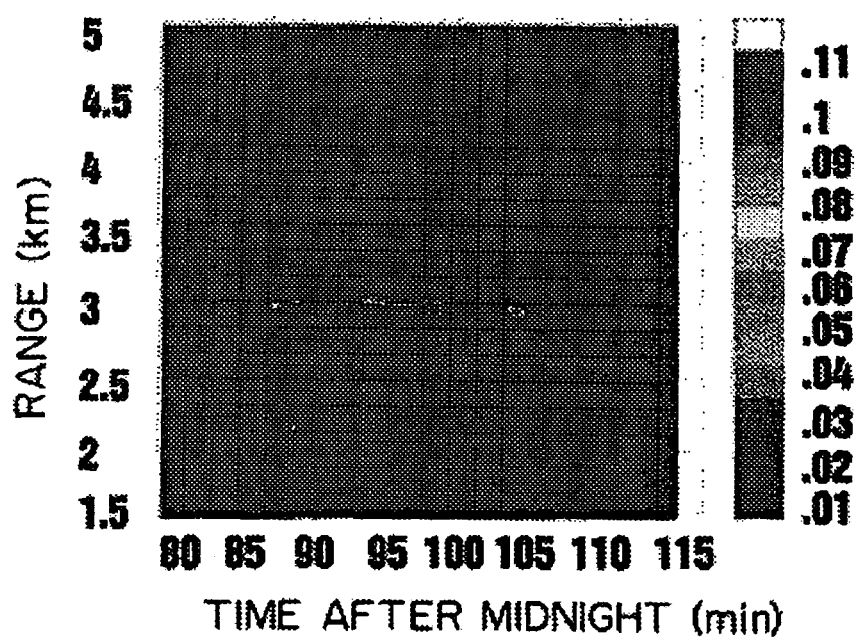

Referring now to the drawings, wherein like reference numerals designate identical or corresponding parts throughout the several views, and more particularly to FIG. 1 thereof, FIG. 1 shows at three wavelengths (i.e., 266, 280 and 355 nm) the reduction in the laser beam intensity due to scattering and absorption by atmospheric constituents as the laser beam travels to a target. Difference in the fluorescence between excitation at 266 nm and 355 nm is more than compensated by the difference in the atmospheric transmittance shown in FIG. 1. From the lidar signal considerations shown in FIG. 1, even with a 100-fold smaller fluorescence cross section, the 355 nm lidar is an exemplary wavelength of choice for the present invention.

In fluorescence lidar, autofluorescence excited by a UV laser from biological cells is utilized to identify the fluorescing biological cells from other non-biological or naturally occurring particles. Naturally fluorescent aromatic amino acids residues which are the intrinsic constituents of nearly all proteins contribute to the fluorescence, as described in Lakowicz, "Principles of fluorescence spectroscopy", Plenum Press, NY, 1984, the entire contents of which are incorporated herein by reference. For the stand-off lidar field application, appropriate candidate UV lasers are fourth and third harmonic diode-pumped Nd:YAG laser, having wavelengths at 266 and 355 nm, respectively. In this excitation wavelength region, the fluorescent bio-molecules are: amino acids—tryptophan, tyrosine, nicotinamide adenine dinucleotide compounds (NADH), and the flavins (riboflavin). The specificity of the spectral signatures from different BW agents is still under debate, see for example Simard, et al, "Active Range Gated Spectrometric Standoff Detection and Characterization of Bioaerosols", Proceedings of SPIE, Vol. 3707, 1999, the entire contents of which are incorporated herein by reference.

However, experiments disclosed in U.S. Pat. No. 6,593,582 have shown that excitation by 355 nm is preferable to that at 266 nm. Furthermore, results by Hargis, et al, "The 440 nm Fluorescence Band of Cultured Bacteria in Solution and on Surfaces," 1998 Scientific Conference on Obsuration and Aerosol Research, Aberdeen Proving Ground, MD 1998, and Hargis, et al, "Results of Multispectral UV Fluorescence Lidar Field Test Measurements at Dugway Proving Ground, Utah and White Sands Missile Range, New Mexico," 2000 MASINT Biological Warfare Science and technology Symposium, Long Beach, Calif., 2000, the entire contents of which are incorporated herein by reference, have also demonstrated that excitation at 355 nm has several advantages. Hence, the induced fluorescence at the 440 nm region is a robust indicator of biological material and is not affected by the growth media used for preparation of the bio-material. On the other hand, the 330 nm band fluorescence (arising mainly from tryptophan) is significantly changed by the growth media. Thus, the 440 nm band fluorescence can discriminate between man-made and naturally occurring bacteria. Also, the smaller atmospheric extinction at both the excitation (355 nm) and fluorescence (440 nm) wavelengths permits a longer range capability as compared to excitation at the 266 nm wavelength. Hence, while not limited to excitation at 355 nm, the lidar system of the present invention can utilize a compact diode-pumped Nd:YAG laser whose third harmonic (355 nm) is used for excitation of the 440 nm fluorescence band and whose residual outputs at the fundamental (1.064 μm) and second harmonic (532 nm) are available for aerosol lidar sensing.

U.S. Pat. No. 6,593,582 describes the selection of appropriate lasers for fluorescence lidar. In accordance with those results, in the present invention, the 440 nm fluorescence is considered to be a robust indicator of biological, cultured material. Since the 440 nm fluorescence band of the bacteria is expected to be weak in naturally-occurring bacteria, while strong in cultured (man-made) bacterial or other bio-agents, the 440 nm fluorescence band represents a way to distinguish man-made from naturally occurring bacteria, leading to the reduction of false alarms in remote stand-off detection instruments.

The wavelength for efficient excitation of fluorescence in bacterial, viral and other bio-agent molecules is the 340-360 nm region, either alone or in conjunction with excitation in the 266-290 m region. Hence, in the present invention, the third harmonic of Nd:YAG laser at 355 nm can be utilized as an excitation source. Recent advances in diode-pumped solid state (DPSS) lasers together with the advances in nonlinear materials have lead to efficient harmonic frequency conversion UV lasers, e.g., frequency tripled (355 nm) and quadrupled (266 nm) diode-pumped Nd:YAG Nd:$YVO_4$ or Nd:YLF lasers with moderately high average powers (up to 5 W in UV) and PRF of 1 to 10 kHz or more are now commercially available. With these lasers, according to the present invention, the fundamental second and third harmonic beams (1.06 μm, 532, and 355 nm) can be utilized for aerosol monitoring.

The appropriateness of these wavelengths (including the appropriateness of 532 nm and 1.06 μm) for the detection of bio-aerosols for the detection of bio-aerosols was described in U.S. Pat. No. 6,593,582. U.S. Pat. No. 6,593,582 described that a sufficient SNR can be obtained at a range up to 20 km for both 532 nm and 1.06 μm wavelengths, with energies that are low enough to maintain an eye-safe, transmitted beam. Field experimental measurements also disclosed in U.S. Pat. No. 6,593,582 of bio-simulant aerosols with a two-wavelength aerosol lidar showed that, in addition to excellent detection sensitivity, preliminary differentiation between several types of aerosols was also obtained. For the 355 nm wavelength the atmospheric extinction is larger, with the result that higher laser energies of the order of 100 to 200 μJ/pulse are required. However, these higher energies do not present much difficulty, because firstly the 355 nm wavelength is also used for fluorescence excitation which requires transmitted pulse energies of the order of 200 μJ/pulse, and secondly the eye-safe energies are also much larger at the UV wavelength.

FIGS. 2A and 2B, reproduced from U.S. Pat. No. 6,593,582, show aerosol backscatter time-series data in the form of false color plots for both the uv and near-IR wavelengths. The x-axis variable is time and y-axis variable is range. The upper trace is the lidar signal reaching the detector as a function of range, and the bottom part is a false color time series plot of the lidar signal amplitude constructed from individual lidar signal data shown in the upper trace. The signal intensity is indicated by the color coding shown on the color bar. The two plots in FIGS. 2A and 2B are raw data aerosol signals for a BG disseminated at a range of 0.8 km, with the wind flowing perpendicular to the line of sight. Hence, the aerosol range is nearly constant, and the intensity is proportional to the aerosol concentration. A differential backscattering signal obtained from the ratio of the signals at the two wavelengths shows significant differences for different types of particles such as: BG, EH (*erwinia herbicola*), kaolin, and road dust. Hence, according to the present invention, preliminary differentiation between natural and disseminated aerosol clouds is made by utilizing this ratio. FIG. 2C-2D, also reproduced from U.S. Pat. No. 6,593,582, show the fluorescence lidar signals measured at 430 nm from the aerosol cloud excited by 355 nm laser pulses.

The lidar system in one embodiment of the present invention includes a transmitter, a receiver, a scanner, an electronics module for data acquisition, and a computer for lidar control, data display and data archival. FIGS. 3 and 4 shows an optical schematic of the lidar system of the present invention including a transceiver optical module 51 and a transmitter/receiver telescope 16. FIG. 4A shows a component layout for the modular lidar system of the present invention.

Two transmitted beams, near-IR and visible are combined using a dichroic mirror into a single beam, which is reflected by a polarizing beam splitter. An UV beam can be independently expanded by a lens and pass through the polarizing beam splitter before being joined to the other near-IR and visible beams by one of the dichroic mirrors. The combined beam is expanded to the full size of the telescope and transmitted into the atmosphere as overlapping beams. The receiver subsystem includes the telescope and four (or more) photodetectors, optionally including pre-detection relay optics, optical and electronic filters, power supplies, and gating electronics. The telescope can be for example a compact Schmidt-Cassegrain 30 cm aperture commercial telescope with UV enhanced aluminium coated mirrors. According to an embodiment of the present invention, the telescope can transmit the overlapping laser beams and receive backscattered and fluorescence signals. Sensors for detection of beams reflected from the atmosphere can utilize dichroic mirrors. A transmitting vector is located co-axially on the receiver axis. The field stops at the focal point of the telescope defines the transmitter optic axis and ensures that the receiver optic axis aligns collinearly regardless of the actual aligment of the rest of the telescope optics. Thus, according to the present invention, coaxial alignment of the transmitter and receiver axes is automatically assured at all time. Assurance of alignment can be an important feature for field operation. Therefore, the present invention can accommodate a significant level of mechanical vibration of the platform during measurement, as well as during transportation.

The small field stops employed and the polarization filtering minimize laser light scattering. The depolarized return signal contains all three elastically scattered components, and the fluorescence, which are separated by the dichroic mirror with a broadband filter and passes through the field stops. Depolarizer or ¼ wave polarization rotators can be used to implement the polarizing beam splitter. Different wavelength signals received in the return signal can be separated by the dichroic mirror and then focused onto the respective photodetectors. Narrow band filters (not shown in FIG. 3A) spectrally centered at the laser wavelengths transmit the unshifted elastic backscattered radiation efficiently (T.about.40%) while rejecting the background solar radiation. A broadband filter (not shown in FIG. 3) centered at 440 nm can be used for the fluorescence channel. A bandwidth of 10 to 20 nm for the broadband filter is adequate, according to the present invention. The broadband filter also provides a greater than $10^6$ fold rejection of the exciting radiation at 355 nm, and a rejection of longer wavelength daylight radiation, λ greater than 450 nm.

According to an embodiment of the present invention, the solar background radiation reaching the detector can be reduced by employing a telescope with a small field of view FOV and narrow band pass filters in the transmitting channels, thus enabling daylight aerosol lidar measurements.

However, the background solar radiation coming through the wider bandwidth of the fluorescence channel at 440 nm can exceed the backscattered or fluorescent signals even for signals being reflected or generated nearby. Although the background can be separately determined and subtracted, the higher photon shot noise can degrade the measurement and in extreme cases restricts an operational range. However, since the viability of bacteria in bright sunlight is very small, bio-agent disseminations are expected to occur under conditions when no significant solar radiation is present. Thus, the lidar system of the present invention can be well-suited for field applications.

As shown in FIG. 4, the laser module 100 includes for example a laser power supply 58, a laser cooling system 56, and a laser source 54. Specifically, FIG. 4 shows a laser 54 such as, for example, a diode pumped Nd:YAG emitting 1.06 μm, 532 nm, and 355 nm laser light. Additionally, diode-pumped solid state DPSS lasers having efficient harmonic frequency conversion, e.g. frequency tripled (355 nm) and quadrupled (266 nm) diode-pumped Nd:YAG or Nd:YLF lasers with moderately high average powers (up to 5 W in UV) and PRF of up to several tens of kHz are commercially available and suitable for the present invention. With these lasers, the fundamental and second harmonic beams (532 nm, and 1.06 μm) can also be utilized. All three laser wavelengths (i.e., 1.06 μm, 532 nm, and 355 nm) can be appropriately beam-shaped using lenses 1-6 shown in FIG. 4A. Alternatively, as shown in FIG. 4A, the laser source 54 is coupled to the transmitter receiver module 102, as shown in FIG. 4A by a coupling mechanism. The coupling mechanism can include in one embodiment of the present invention a laser fiber optic cable 106 permitting the laser source 54 to be remotely coupled to the lidar system.

The detection system 52 shown in FIG. 4A can include Si-based avalanche photodiodes APD and photo multiplier tubes PMTs (either multi dynode type or channel multipler types) can be utilized for detectors. Typically, a Si-APD detector quantum efficiency is approximately 15% at 440 nm, greater than 50% at 532 and, and approximately 70% at 830 nm, and decreases to less than 3% at 1.06 μm. Quantum efficiency of conventional PMT is approximately 20% at 440 nm, and 10 to 15% over the visible, decreasing quickly for the infrared. All detector channels can, according to the present invention, utilize Geiger mode Si APD single photon counting modules. However, the fluorescence and the UV scatter signals utilize UV PMTs operating in a photon counting mode.

The field stop apertures shown in FIG. 4A limit the telescope FOV and provide geometric compression of signal for all channels, and prevent detector overloading from an initial scattered signal in the near field. The size of the aperture and the transmitted beam divergence serve to compress the dynamic range of the lidar signal. Furthermore, according to the present invention, the detectors can be gated off for a short period following the laser-pulse transmission to avoid an after-pulsing effect which can cause detector overload. An optical Q-switch can be applied in front of the detectors to filter initial scattered light as well as near-field signals. Small portions of the three outgoing beams are collected for energy monitoring of the photo-diodes and signal normalization.

Light scattered by the optical components in the transmitter constitutes a significant part of the signal reaching the detector. For example, knowing that the highest count rate of most detectors is of the order of $10^7$ counts/sec and that 1 μJ output of a 1047 nm laser pulse contains $5.27\times10^{12}$ photons, even a very small fraction (say $10^{-9}$ of the pulse) will saturate the detector many times over because the pulse is very short (~10 ns). The scattered light originates from intrinsic scattering within the optical material (such as glass) in addition to imperfections or foreign particles (such as, bubbles) embedded inside, and from the surfaces which are commonly coated with antireflection, partial or fully reflective coatings). The intrinsic or Rayleigh scattering is present in all materials and it increases as ($1/\lambda^4$) i.e., the intrinsic scatter in the 355 nm UV wavelength is 81 times stronger than that for near IR 1064 nm. Although the scattering from inclusions and surfaces can be reduced substantially by using the highest quality substrates and optical coatings, it cannot be completely eliminated.

Since the internal scattering from transmitter components will always be present in the common transmitter/receiver geometry, an embodiment of the present invention utilizes a number of optical schemes (described below) that either mitigate or completely eliminate the high initial signal pulse from affecting the lidar measurement. In addition, the transmitter can be enclosed by an enclosure to provide an hermetic seal for the optical components in the transmitter from atmospheric gasses. Further, a desiccant can be included in the enclosure to remove moisture from an interior of the enclosure.

In one embodiment of the present invention, a second independent (smaller) telescope for collecting the atmospheric scattered light is used. By displacing the transmitting aperture from the receiver aperture, the overlap between the field of view of the two apertures can be adjusted to start only after a few tens of meters away so as to avoid collecting returns for the first few tens of nsec. This approach is well suited for the UV wavelength channel, because the ($1/\lambda^4$) dependence of internal scattering affects the UV wavelength channel much more than the near-IR wavelength channel.

In another embodiment of the present invention, detector saturation is avoided or reduced, as showed in FIG. 4B, by a high speed acousto optic deflector (AOD) employed to deflect the return signal beam collected by the telescope away for the detector into a beam dump for a short duration. FIG. 4B is a schematic of an acousto-optic deflector used to deflect a large part of the received beam into a beam dump for the initial part of the return signal. The initial part (for the first 200 to 500 ns) of the return signal pulse can be relatively strong due to the strong internal scattering from the lidar optical components and the signal received from near range aersosol scattering from atmosphere reaching the detector. By dumping this initial part of the return signal, the detector does not suffer from an signal overload.

Acousto-optic deflectors are commercially available and provide deflection efficiency of up to 90% and have a very rapid response time (~100 ns). For example, by preventing the beam from falling on the detector for 0.5 μs, the strong signal from the first 75 m is prevented from falling on the detector. In the present invention, the AOD can be used either in the configuration shown in FIG. 4B or in a complementary configuration where the detectors are placed in the deflected light beam path. In the former situation, the AOD is turned “on” position to block light to detector and turned “off” to let the full signal to reach photodetectors. In the latter configuration, AOD modulator is turned “on” after the first ~0.5 μs for the full duration of signal measurement. This configuration provides improved immunity for the initial strong peak pulse over the former configuration.

As shown in FIG. 4, the data acquisition and analysis system 50 includes programmable multichannel scalers (MCS) directly connected to the detector modules. Range bins of the MCS are selectable between 10 nsec (e.g. for 1.5 m range resolution) and 2 μsec (e.g. for 300 m range resolution). The data acquisition and analysis system 50 can also include a computer to control the laser operation, the gating of the detectors, acquisition of energy monitor data, and lidar signals. Time integration of the lidar return signals can be performed by the MCS units, and the averaged data can be read at a predetermined rate by a processor in the MCS and transmitted to the computer.

According to an embodiment of the present invention, an effective algorithm for rapid analysis of the aerosol signals and identification of suspect aerosol clouds is incorporated in the computer for real-time operation applications. Upon confirming the presence of bio-particles in the aerosol cloud, an automatic alarm can be generated. Further processing of the signal is done on the computer. The computer can feature real-time, range-intensity display of the signal data.

For the effective use of a biological stand-off sensor, the sensor preferably detects the BW agent aerosol cloud at as far away as 5 km so that there is adequate time to warn. Further the sensor preferably provides a clear discrimination of the cloud of whether the cloud is a bio-threat or not. The non-threat clouds can be other aerosols such as dust, vehicular smoke, non-toxic bio materials including pollen, or deliberately introduced interferents or obscurants. Hence a real-time analysis of the lidar can be performed to detect, track and discriminate all aerosol clouds in the field of view of the lidar.

Figure 4:
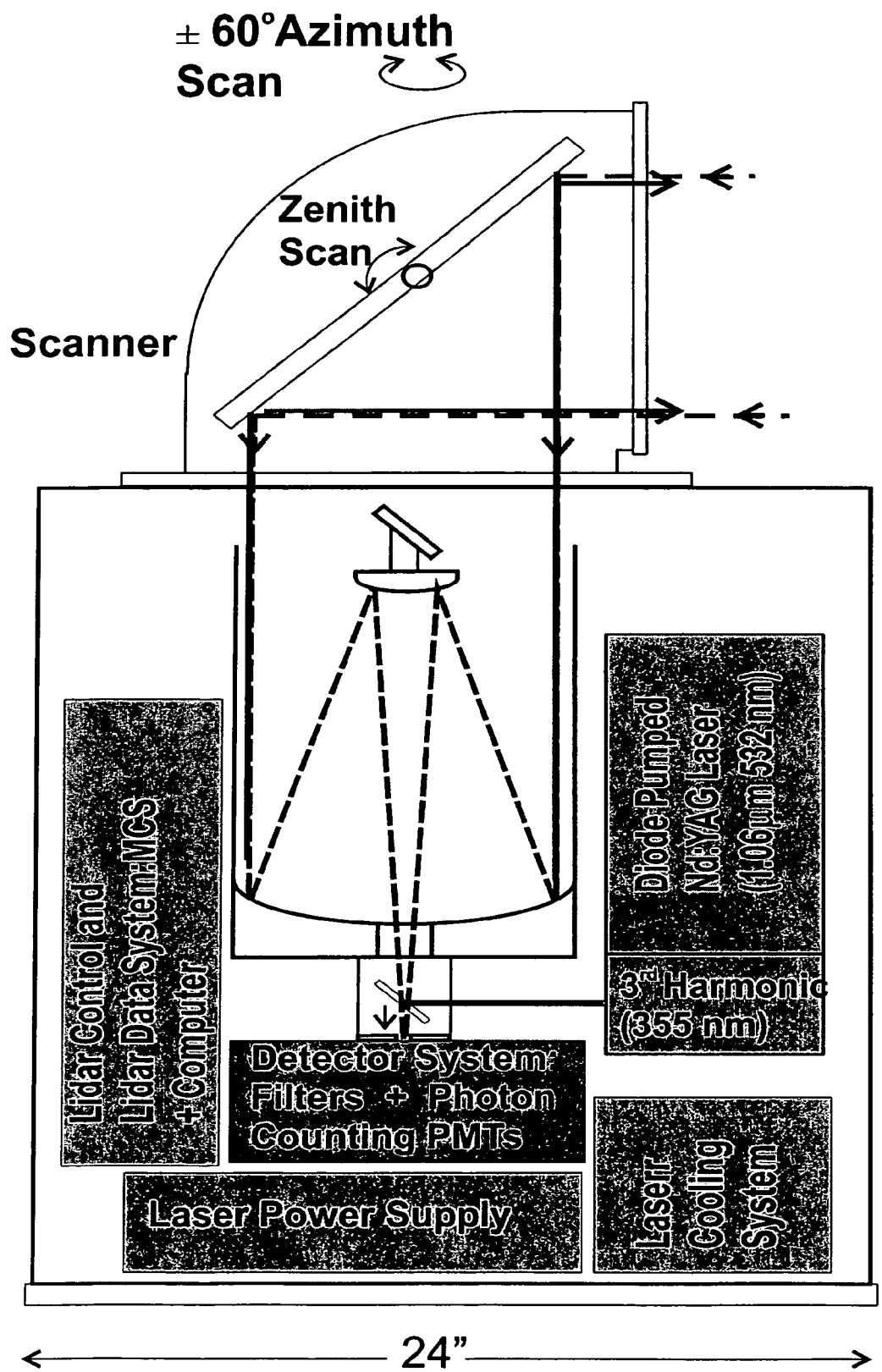
FIG. 4 is an optical schematic of a lidar system including a scanning mechanism according to an embodiment of the present invention.

In one embodiment of the present invention, the data acquisition and analysis system 50 utilizes an analytical procedure and an algorithm to analyze the lidar data in real-time to detect and track aerosol clouds in the atmosphere, and then discriminate the aerosol clouds as bio- or non-bio clouds. Each of these tasks can be separated into an independent analysis modules. The algorithm integrates these modules appropriately for real time analysis of the lidar data and to report critical data to the operator, as for example detailed false color images in addition to both visual warning and audible alarms depending on the outcome of detection and discrimination. Despite the relative complexity of the analysis and the multitude of computations that are used, the algorithm can run on the Windows 2000 platform and achieve real-time operation. The algorithms shown in FIGS. 4C and 4D have been demonstrated using Visual C++ and have been implemented on a Pentium based laptop computer.

Individual of the analysis modules can utilize high speed statistical procedures in conjunction with digital filtering and other mathematical procedures. The complete lidar program can include a shell program containing an operator interface, graphical displays of real time raw and processed data, a 2-dimensional false color cloud image in a radial (radar scope-like) format, in addition to the high speed algorithm that performs the data analysis. To reduce the burden on the data system computer, the MCS data acquisition module can preprocess some of the data by accumulating lidar data for one averaging period, unlike the conventional lidar systems where data from every pulse is processed and archived.

According to an embodiment of the present invention, the eye-safety requirement can be met by expanding the transmitted laser beams to the full aperture of the telescope so that the power density of the transmitted beams is reduced below the eye-safe limit. The maximum permissible exposure (MPE) for a pulse laser is based on the peak power of the pulse, while the MPE for a cw system concerns the total energy for an extended exposure period depending on the eye aversion, which is a fraction of a second for visible light and a few seconds for the UV and IR lasers.

Figure 3:
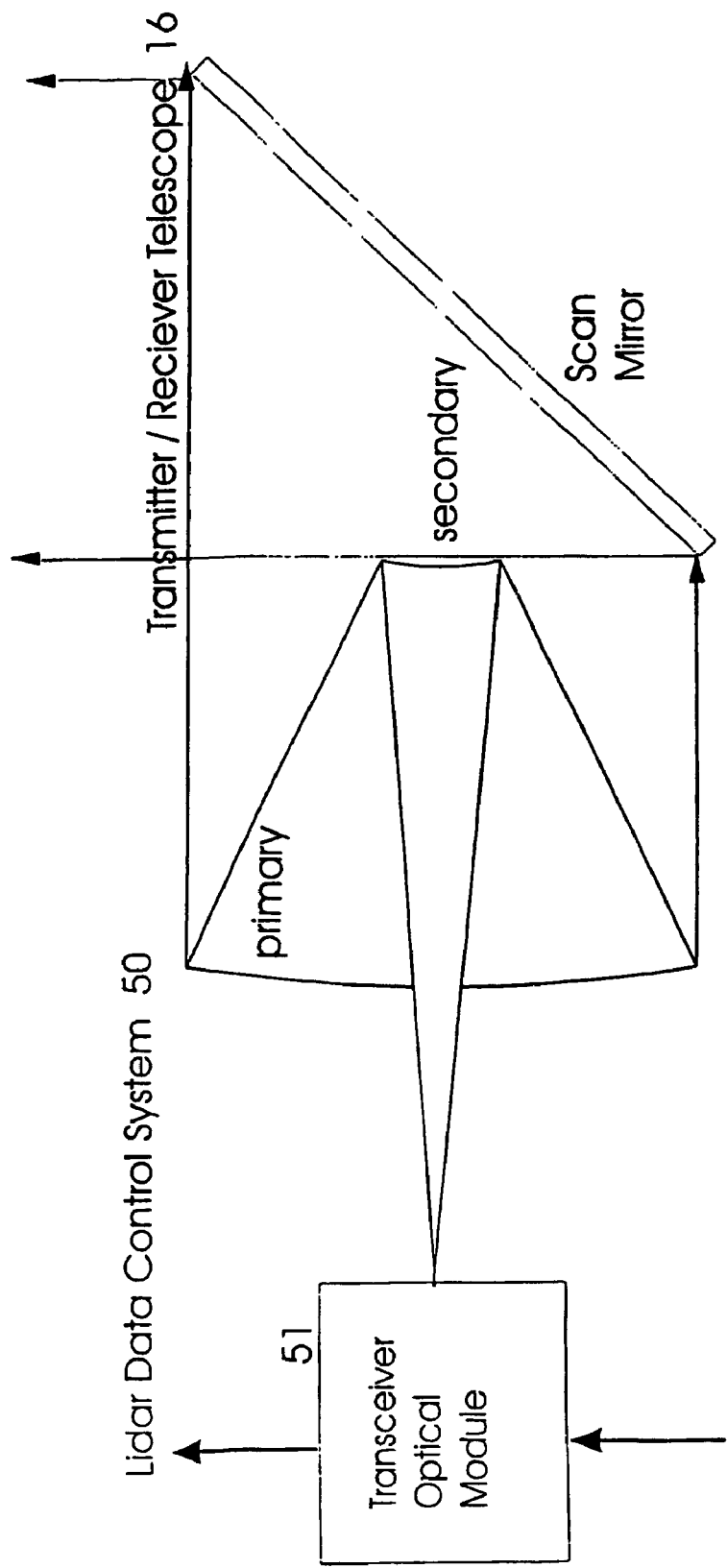
FIG. 3 is an optical schematic of a lidar system including a transceiver optical module and a transmitter/receiver telescope.

The MPE for repetitive pulses in the visible wavelengths with a PRF of N is reduced from the MPE of a single pulse by a factor of $N^{-1/4}$. Since the reduction of MPE is a rather slow function of the pulse repetition rate while the average power increases linearly with the pulse repetition rate, the eye-safe lidar system of the present invention preferably utilizes a high PRF low pulse energy laser transmitter which provides comparable average output power. The signal information content can be linearly proportional to the average power by filtering the noise contribution. Thus, according to an embodiment of the present invention with filtering capabilities, the laser beam upon expansion by a telescope 16 (such as for example telescope 16 in FIG. 3) can satisfy the ANSI eye-safety requirement.

To illustrate compliance with this standard, MPE values have been computed for the different laser beams. As an example, MPE value for a 532 nm single pulse is $\sim 5 \times 10^{-7}$ $J/cm^2$, which becomes $1.06 \times 10^{-7}$ $J/cm^2$ for 500 pulses (0.25 sec eye-blink response exposure of a 2 kHz laser) by the $N^{-1/4}$ law. Therefore, by expanding the beam in a 30 cm telescope, as described in U.S. Pat. No. 6,593,582, this expansion translates to a 69 µJ pulse energy which satisfies the MPE requirement. For 355 nm, the MPE value is 1 $J/cm^2$ for a single pulse, thus producing a 4.2 $J/cm^2$ for 10 sec exposure of a 2 kHz laser according to the $N^{-1/4}$ law. Even if the $N^{-1/4}$ law is not applicable to the UV exposure, the direct cumulative 1 sec exposure (2000 pulses) at 1.5 mJ amounts to energy density of only 4.3 $mJ/cm^2$, for the 30 cm transmitter, which is well below the MPE of 1 $J/cm^2$.

Although the transmitted beam can be eye-safe for the normal unaided eye, it can present a potential hazard for aided vision, such as what occurs when persons using magnifying optics e.g., binoculars, stare at the transmitter. Taking a 7× magnification binoculars it is computed that the maximum transmitted pulse energy is preferably ~3 µJ for a totally eye-safe beam (NOHD=0 m) of 1047 or 1064 nm wavelength, when the transmitter beam is 31 cm diameter and laser PRF is 10,000 Hz. For the UV (355 or 266 nm wavelengths), the hazard is not increased because most binoculars use glass lenses which do not transmit UV light.

Figure 4A:
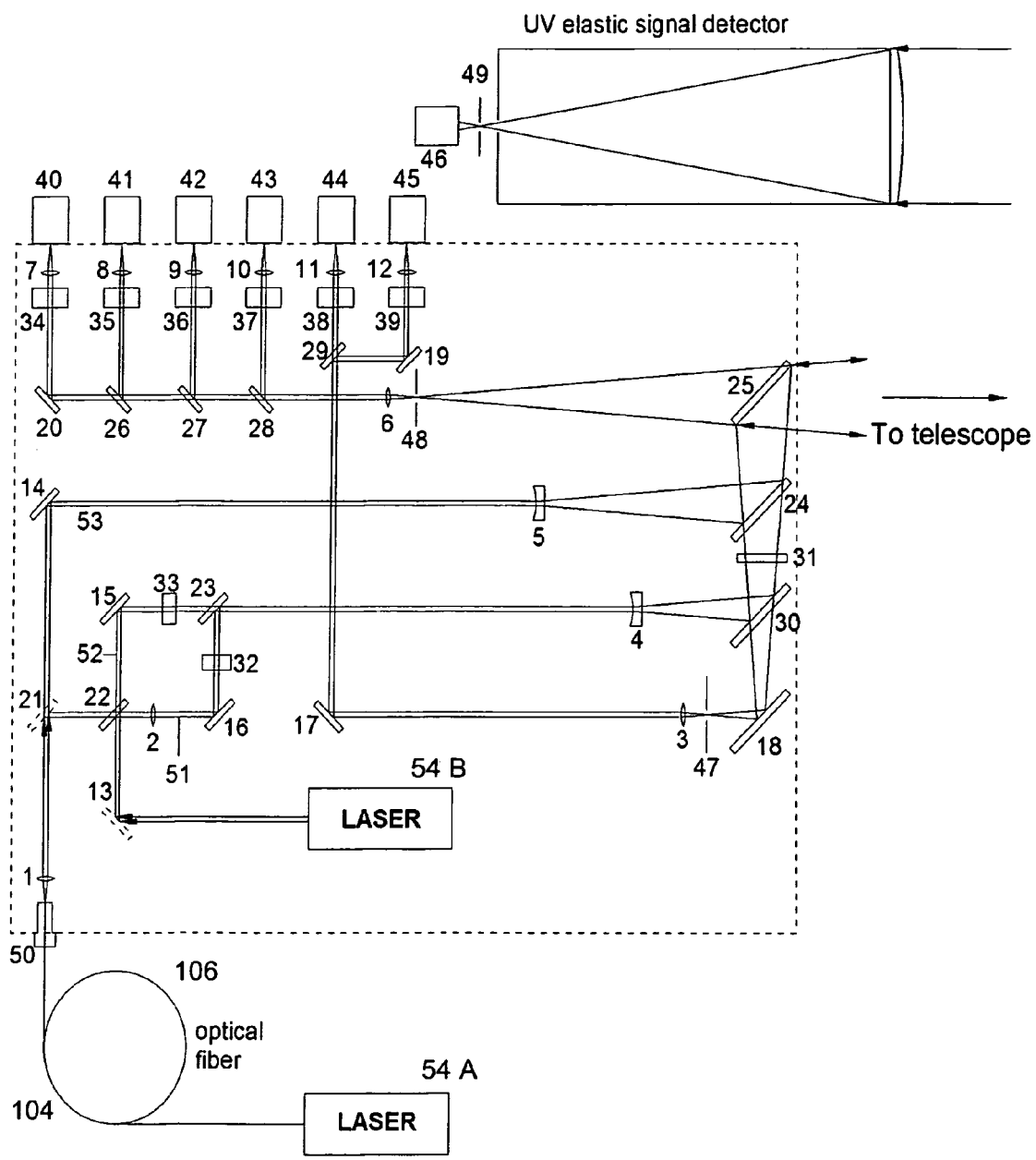
FIG. 4A is an optical schematic of a transceiver optical module according to an embodiment of the present invention.
Figure 4B:
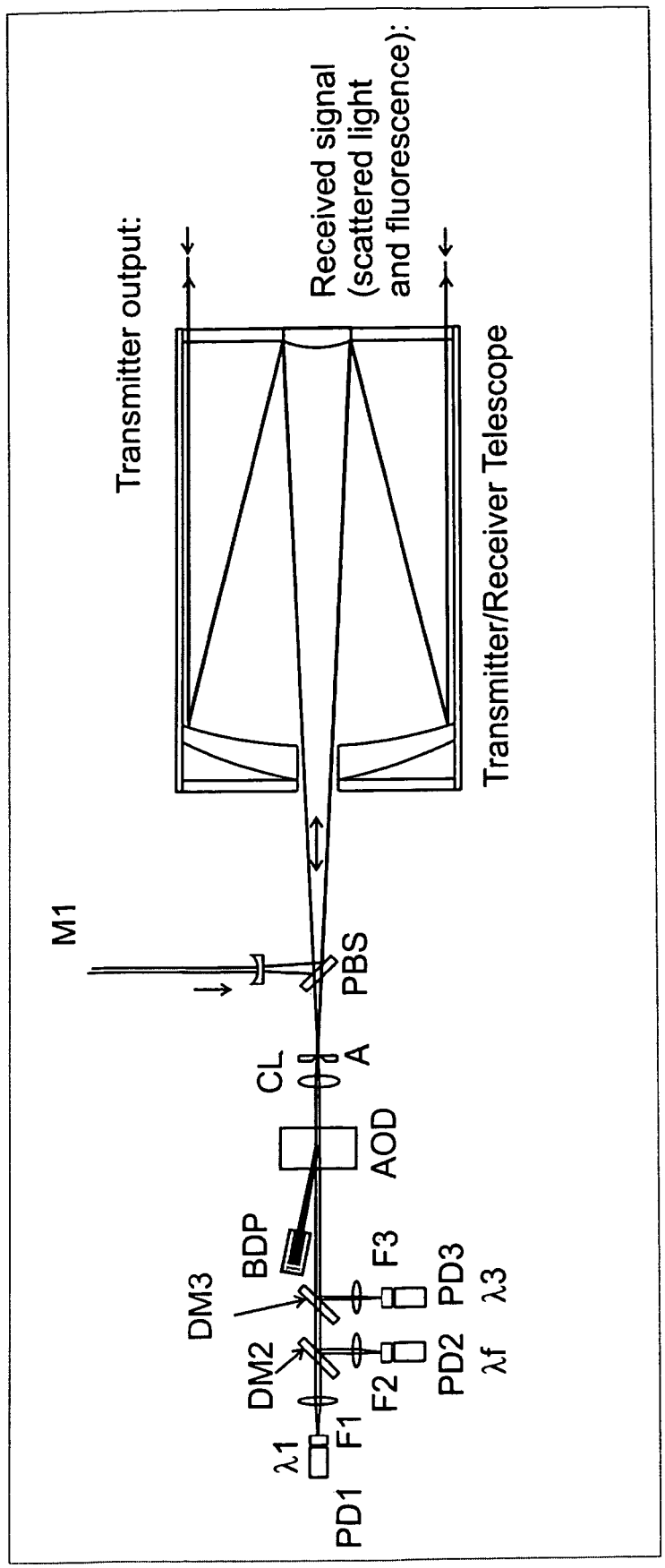
FIG. 4B is an optical schematic of a component layout for the lidar system according to an embodiment of the present invention utilizing a optical deflector and a beam dump.
Figure 4:
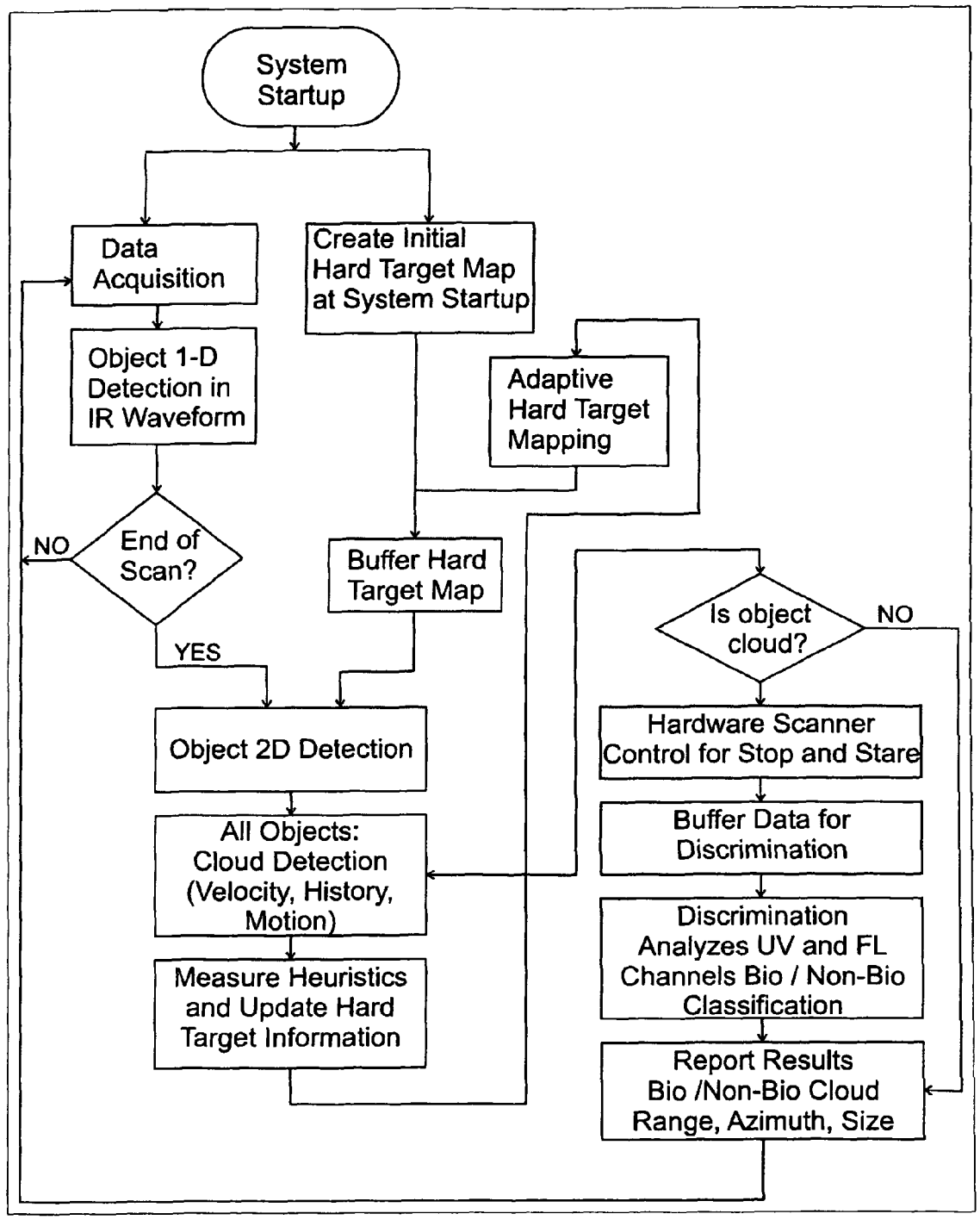
Figure 4D:
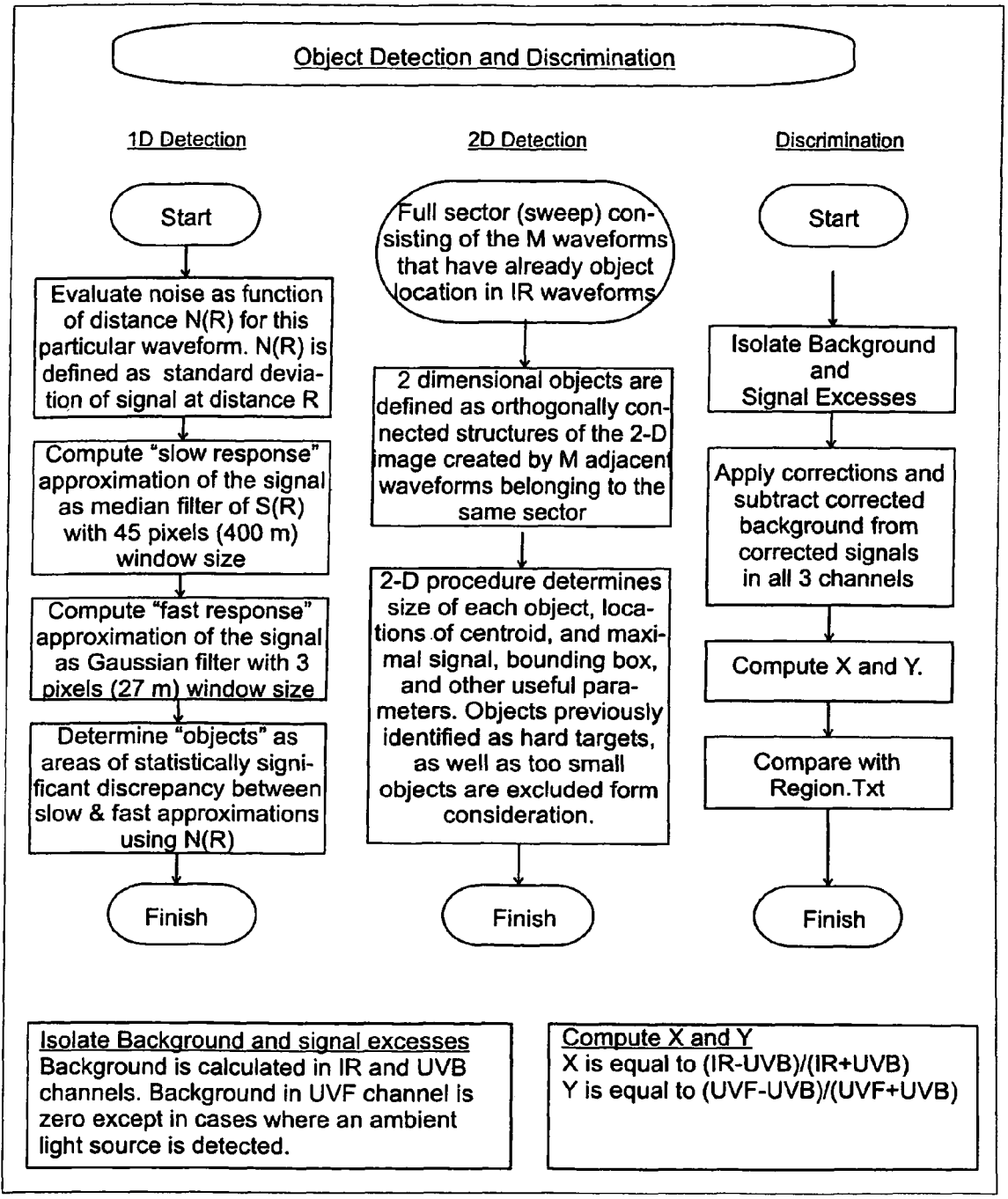
FIG. 4D is a flow chart illustrating further one computer-implemented method according to an embodiment of the present invention for analyzing the digital lidar signature.

The sensitivity of the lidar can be considerably reduced when the transmitted energy is limited to 3 µJ/pulse, 10 kHz. In one embodiment of the present invention, a procedure is utilized by which it is possible to increase the transmitted energy and still maintain eye-safe lidar operation. Since UV laser light is eye-safe, it can be used to detect any intruder wandering into the transmitted laser beam by using a threshold detector in a separate UV channel such as shown in FIG. 4A. Whenever a person or other objects move into the beam field of view, a signal to rapidly (e.g., in less than a few µsec) attenuate the non-eye safe near-IR laser beam is sent to a transducer that is placed in the IR laser beam. Such a transducer is shown as element in FIG. 4A. The transducer can be a high speed acousto-optic deflector (such as the AOD shown in FIG. 4B) placed in the near-IR laser beam path, which can be turned on to rapidly (<1 µsec) to deflect a large part of the near-IR laser beam into a beam dump, and transmit a small part of the beam (e.g., 3 µJ/pulse) that is eye-safe even for binocular assisted vision.

Elastic scattering signal strength depends on the relative size parameter $\varsigma$, (defined as the ratio of the perimeter of the particle to the wavelength $\lambda$, i.e., $\varsigma = 2\pi a/\lambda$, where a is the radius of the scattering particle), and the absorption coefficient of the particles $\alpha(\lambda)$, at the laser wavelength. Thus, use of widely separated laser wavelengths provides a differential scattering signal that can be effectively used to classify the aerosol particle size. For example, knowing that the sizes of the normal atmospheric aerosols are usually in the sub-micron range, any aerosols that are in the >1 µm (say between 1 and 10 µm) size will be expected provide a substantially different elastic scatter signal when the excitation wavelengths are 355 nm and 1064 μm. Also it should be noted that it is not essential to use only the 1.06 μm (or the 355 nm) wavelength. Instead lasers with other wavelengths in the 970 to 1.1 μm (340 to 380 nm) could be substituted. This allows the use of semiconductor diode lasers whose outputs cover these ranges. Furthermore, other wavelengths which are more widely separated can also be considered to enhance the power of differential scattering.

Analysis and comparisons for discrimination between natural and man-made aerosols, the bio-aerosol simulant, *bacillus globigii* (BG) were described in U.S. Pat. No. 6,593,582. The minimum detectable concentrations were determined by taking the $SNR_{min}=4$. For 266 nm, excitation at 5 km range, a minimum detectable concentration of $2\times10^4$ ppl is estimated, whereas for 355 n, even at 7 km the minimum detectable concentration is better than $1\times10^4$ ppl. This supports the position that the performance of the lidar system of the present invention can provide performance adequate for standoff detection of a BWA cloud at a distance required for military operations.

The atmospheric extinction can be calculated assuming a visibility of 23 km. To prevent overloading the detector with the strong near field signal, geometric compression can be incorporated in the form of a field stop (250 μm) at the focal point of the receiver optics. The size of the image formed by the telescope at its focus is a function of the range and reduces quadratically with the range until reaching the diffraction limit at a large range. By using a small pinhole, only a small part of the near field return signal falls on the detector. The image size becomes smaller than the 250 μm pinhole for range >3 km for the f/10 telescope. Thus, geometrical compression occurs for the first 2.5 km limiting the light falling on the detector and the full amount of signal subtended by the telescope aperture is transmitted through the aperture and received by the detector for the ranges beyond 2.5 km. In FIGS. 5, 6, and 7, the effect of geometric compression is shown for the near-field range where the signal is nearly flat.

The lidar system of the present invention can include a laser source 54 which provides laser pulses of at least two wavelengths, a transceiver optical module 51 including transmitter (shown as the lower half components in FIG. 4A) which transmits the laser pulses, a receiver (shown as the upper half components in FIG. 4A) which receives both elastically backscattered signals from airborne agents and fluorescence signals from the airborne agents, a telescope (such as for example telescope 16 in FIG. 3) which both focuses a laser beam transmission of the laser pulse from the transmitter to a far field and receives the elastically backscattered signals and the fluorescence signals from the far field, a digital detection system 52 having at least one of a backscatter optical detector which detects a presence of the airborne agents by detecting elastically backscattered signals and a fluorescence optical detector which detects the fluorescence signals from the airborne agents.

The receiver is configured with a focal point of the receiver located at a conjugate point of a focal point of the transmitter. The lidar system of the present invention can include, as shown in FIG. 4, a frame 60 which rigidly mounts optical components of the transmitter, the receiver, and the telescope and which maintains a predesignated direction of the laser beam transmission against vibration and shock of the system. Further, the lidar system can include an azimuthal and zenith scanning device 62 which scans by moving the laser system in an enclosure 64 supported on an axle and fork structure (not shown in FIG. 4).

The laser pulses can include at least one of a 1.06 micron (or other wavelength in the 970 to 1.1 micron range) wavelength pulse, a 532 nm (or other wavelength in the 525 to 535 nm range) wavelength pulse, and a 355 nm (or other wavelength in the 340 to 370 nm range) wavelength pulse. The laser can pulse with an energy of the order of 1 mJ (a few hundred μJ) at the 355 nm wavelength pulse and of the order of hundred μJ (tens to hundred μJ) at the 1.06 micron wavelength pulse and the 532 nm wavelength pulse. The laser can pulse with a repetition rate of a 1-10 KHz. The transmitter (i.e. the azimuthal and zenith scanning device 62 and the telescope 16) can be configured to transmit the laser pulses coaxially and to expand the laser pulses with the telescope 16 such that the laser beam transmission is eye-safe.

The receiver can include an optical separator with a beam splitter which separates the elastically backscattered signals and the fluorescence signal. The beam splitter can include dichroic beam splitters to spit the elastically backscattered signals and the fluorescence signals. The transmitter in the transceiver optical module 51 can transmit a laser pulse in a 340 to 360 nm wavelength region to induce a fluorescence signal in a 440 nm wavelength region. The receiver can include the zimuthal and zenith scanning device 62 as an angular positioning device configured to position a focal point of the receiver to maximize the long-range return signal. The angular positioning device can be motorized and have position encoders for records.

The transmitter, the receiver, and the telescope can suppress light interference from internally scattered laser light through utilization of variable size apertures 31, 32, 33 which define a field of view at a focal point of the receiver and may be located at a maximum distance from sources of internal scatter to suppress light interference from internally scattered light. The transmitter can be configured to have a compressed dynamic range. Suppression of light interference in the present invention can be obtained by locating an optical baffle between the receiver and the backscatter optical detector or the fluorescence optical detector, by using a polarizing beam splitter 9, 15 or a rejection filter (e.g., a dichroic beam splitter located in front of the backscatter optical detector or the fluorescence optical detector), and by using high-grade UV optical components which minimize extraneous fluorescence that could be generated by laser light transmission through optical components such as for example, lenses with fluorescent optical bands.

In one embodiment of the present invention, the backscatter optical detector or the fluorescence optical detector can include an optical Q-switch in front of the detector to temporarily filter the elastically backscattered signals and the fluorescence signals. The backscatter optical detectors and the fluorescence optical detector can utilize avalanche photodiode detectors such as for example a solid state Geiger mode detector. In another embodiment, an optical fiber matched by aperture size can couple a signal from a receiver focal point to the backscatter optical detector or the fluorescence optical detector.

The laser source 54 can provide three wavelengths, i.e. a fundamental wavelength, a second harmonic wavelength, and a third harmonic wavelength. For example, the laser 54 could be a solid state laser such as a Nd:YAG laser, a Nd:YLF laser, a ND:YVO4 laser, and an Yb:YAG laser producing laser light at a fundamental wavelength of 1.064 μm, 1.047 or 1.053 μm, 1.064 μm, and 1.03 μm, respectively, a second harmonic wavelength of 532, 523 or 527, 532 and 515 nm, respectively, and a third harmonic wavelength of 355, 349 or 351, 355, and 343 nm, respectively. In one embodiment of the present invention, the laser can be tunable for differential lidar measurements of atmospheric trace gases. In another embodiment, the modular lidar system can include a Raman filter to resolve Raman scattering from specific atmospheric gases.

The lidar system of the present invention can include in the data acquisition system 50, a computer to analyze the backscattered signals to for example determine size distribution information, to analyze the fluorescence signals to determine an identity of the airborne agent, and to analyze the fluorescence signals to determine if the airborne agent is a bio-warfare agent. The computer can differentiate the bio-warfare agent by measuring multiple band fluorescence signals within a broad fluorescence band. The computer can differentiate naturally occurring aerosols from the bio-warfare agent by analyzing the elastically backscattered signals from laser pulses of at least three wavelengths. The computer can differentiate naturally occurring aerosols from the bio-warfare agent by analyzing information on a time evolution of a size of an aerosol cloud and a settling rate of the aerosol cloud. The computer can determine a wind speed and direction of the aerosol cloud by the size and settling rate of the aerosol cloud.

The computer can differentiate naturally occurring aerosols from the bio-warfare agent based on fluorescence signal data in conjunction with wavelength backscattering data from laser pulses of at least three wavelengths. The computer can differentiate naturally occurring aerosols from the bio-warfare agent by switching between a scanning mode to detect suspicious aerosol clouds at long-range and a non-scanning mode for high sensitivity fluorescence detection. The non-scanning mode utilizes fluorescence measurements in a single fluorescence filter band to provide a general indication of a presence of the bio-warfare agent in the suspicious aerosol cloud and utilizes multiple spectral bands for specific identification of the biological warfare agent or a class of biological warfare agents. The single fluorescence filter band can be restricted to a band 10 to 20 nm wide. The multiple spectral bands can include bands 2 to 5 nm wide.

The lidar system of the present invention represents a compact and robust aerosol and fluorescence portable digital lidar for stand-off detection and discrimination of biological and chemical-warfare agents. The system can utilize digital detection to provide high sensitivity and excellent range capability. A single commercial laser with modest energy requirements (<1 mJ at 355 nm, 0.2 mJ at 532 m and 0.5 mJ at 1064 nm) is adequate. The resulting lidar system is low cost and robust for field use. Performance simulations for an embodiment of the present invention have shown a better than 7 km range for the fluorescence lidar and a 20 km range for the aerosol lidar. Minimum detectable concentrations are ~1000 ppl at 1 km and $10^4$ ppl at 5 km. These detectable concentrations agree closely with the results of other internal experiments by the present inventors where about 1300 ppl was obtained for 600 shot average at 1 km. By averaging over 10000 shots (only 1 second for the laser), the sensitivity improves to 325 ppl. Scanning at angular speeds of 2 to 5°/sec is possible so that a full sweep over a .±.60°. angular range can be accomplished in 1 minute or less.

Figure 5:
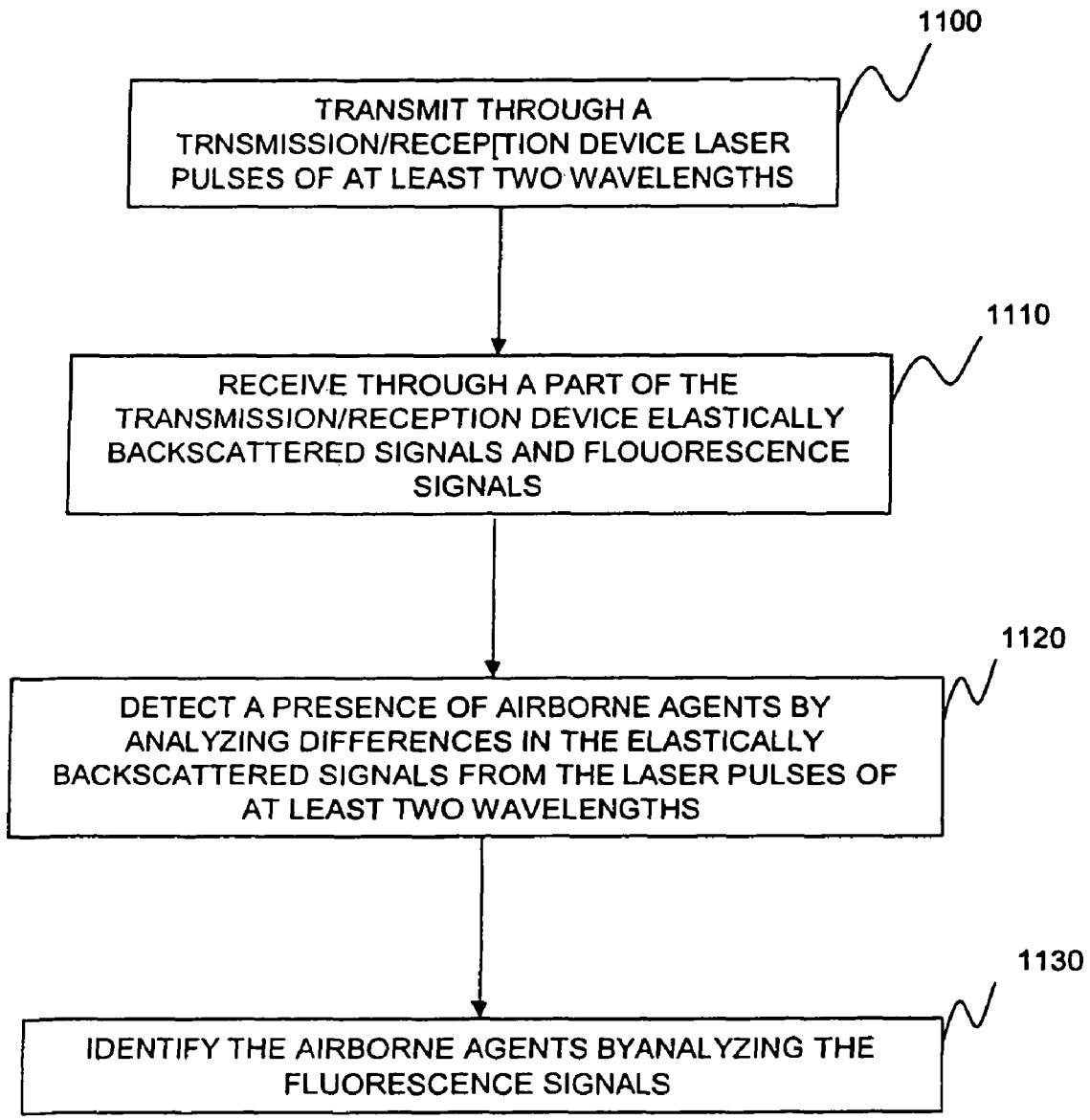
FIG. 5 is a flow chart illustrating a method according to an embodiment of the present invention for detecting an airborne agent.

FIG. 5 depicts a flow chart illustrating a method for detecting airborne agents (and corresponding means for detecting airborne agents) such as for example biological warfare gas agents, according to an embodiment of the present invention. The method includes the following steps (or means). At step 1100, laser pulses of at least two wavelengths are transmitted from a laser source through a remote coupling mechanism and through a transmission/reception device (e.g. the transceiver optical module 51). At step 1110, elastically backscattered signals and fluorescence signals are received through a part of the transmission/reception device (e.g., a common telescope 16). At step 1120, the presence of airborne agents is detected by analyzing differences in the elastically backscattered signals from the laser pulses of the at least two wavelengths. At step 1130, the identity of the airborne agents is determined by analysis of the fluorescence signals.

Correspondingly, steps 1100 and 1110 include aligning autonomously the telescope with transmitter and receiver optics in the transmission/reception device. The step of aligning autonomously can position a receiver field of view aperture at a conjugate point of a transmitter focal point across from a corresponding beam splitter to maximize a reception of the elastically backscattered signals and the fluorescence signals from a far field.

The step of transmitting at step 1100 can pulse a laser with at least one of a 1.05 micron wavelength pulse, a 525 wavelength nm pulse, and a 350 nm wavelength pulse, can pulse with an energy of at least 1 mJ at the 350 nm wavelength pulse and pulse with an energy of at least a few hundred µJ at the 1.05 micron wavelength pulse and the 525 nm wavelength pulse, can pulse with a repetition rate of 1-10 KHz.

Further, the step of transmitting at step 1100 can transmit the laser pulses coaxially and expand a laser beam of the laser pulses such that a laser beam transmission is eye-safe, can transmit a laser pulse in a 340 to 360 nm wavelength region to induce a fluorescence signal in a 440 nm wavelength region, can transmit a tunable laser pulse suitable for differential lidar measurements of atmospheric trace gases, and can steer the transmitted laser pulses by scanning in azimuthal and zenith directions.

The step of receiving at step 1110 can filter temporarily the elastically backscattered signals and the fluorescence signal, can filter at least one of the elastically backscattered signals with a Raman filter to resolve Raman scattering measurements of specific atmospheric gases, and can position a receiver field aperture at a focal point of the receiver to maximize a long-range return signal. The elastically backscattered signals can be filtered to determine size distribution information, can analyze the fluorescence signal to determine an identity of the airborne agent, can analyze the fluorescence signal to determine if the airborne agent is a bio-warfare agent, can differentiate the bio-warfare agent by measuring multiple band fluorescence signals within a broad fluorescence band, can differentiate naturally occurring aerosols from the bio-warfare agent by analyzing the elastically backscattered signals from laser pulses of at least three wavelengths, can differentiate naturally occurring aerosols from the bio-warfare agent by analyzing information on a time evolution of a size of an aerosol cloud and a settling rate of the aerosol cloud.

Further, the steps of detecting and identifying at steps 1120 and 1130 can determine a wind speed and direction of the aerosol cloud by the size and the settling rate, can differentiate naturally occurring aerosols from the bio-warfare agent based on fluorescence signal data in conjunction with elastic backscattering data from laser pulses of at least three wavelengths, can differentiate naturally occurring aerosols from the bio-warfare agent by switching between a scanning mode to detect suspicious aerosol clouds at long-range and a non-scanning mode for high sensitivity fluorescence detection, and can differentiate naturally occurring aerosols from the bio-warfare agent by utilizing fluorescence measurements in a single fluorescent band to provide a general indication of a presence of the bio-warfare agent in the suspicious aerosol cloud and utilizes multiple spectral bands for specific identification of the biological warfare agent or a class of biological warfare agents.

Thus, the lidar system of the present invention maximizes the signal-to-noise ratio (SNR), thus maximizing the range capability for a given SNR. An acceptable criterion for the confident detection of BW agent aerosol in the atmosphere is for the signal-to-noise ratio of the lidar signal to be about four. In addition to photon shot noise generated by the laser scattered light falling on the detector, a detection system itself can contribute to the noise.

In a conventional lidar system, where analog detection technique is used, the noise depends on the detector dark noise together with the signal shot noise, i.e., the noise in the associated amplifier and the detection bandwidth. The bandwidth of a lidar system is determined by the desired spatial resolution of the lidar measurement. For example, a 15 m spatial resolution requires at least 5 MHz bandwidth. The minimum signal required for an analog lidar system to successfully measure an aerosol is determined by the detector dark current and the bandwidth. Thus, in the analog lidar design approach, increasing the measurement range requires increasing the signal, which normally implies a high-energy laser and a large telescope for collecting the signal. For the BSDS system previously discussed, a laser energy >100 mJ, and a telescope receiver size of 65 cm dia. is utilized.

In contrast, the lidar (PDL) system according to an embodiment of the present invention can utilize digital detection, where the detection noise is minimized so that a much lower signal level is adequate to yield the required SNR. Digital detection utilizes photon-counting which generates digital pulses for every photon that is detected and is not affected by the bandwidth or the amplifier noise. As previously noted, in one embodiment of the present invention, a Geiger mode avalanche photodiode (APD) detector is utilized with low signal induced noise. Other than the photon shot noise, the only noise source in digital detector is the detector dark count noise, which is about three orders of magnitude smaller than the dark current noise in an analog detector.

Hence, digital detection system is capable of detecting signals nearly a thousand times smaller than analog detection. Thus, the laser energy for the fluorescence excitation can be reduced to ~0.5 to 1 mJ, allowing smaller laser sources or allowing greater range and detection sensitivity for a given laser source. As a consequence, the laser size and cost for performance are reduced by nearly a factor of ten. Further, the laser sources can operate at high pulse repetition frequency (PRF) of a few tens of kHz without significantly increasing cost or size. Averaging multiple shot data improves the SNR (as the square root of the number of pulses). By averaging over many thousands of shots, the useful range of the lidar is extended as the SNR at the extended range becomes acceptable within a few seconds. While the SNR of an analog lidar detector can be improved by signal averaging, increasing the PRF of a analog-suitable laser (e.g., a 100 mJ laser with a repetition rate of 30 Hz) can be relatively expensive and difficult.

The digital lidar system of the present invention is equipped with a scanner to cover a wide angle (up to ±180°) for simultaneously monitoring multi-wavelength elastic scattering and laser-induced fluorescence from aerosols. Tracking of cloud and aerosol packets by rapidly scanning over a wide field of view allows the wind direction and speed to be obtained continuously. The concept of using a single $3^{rd}$ harmonic Nd:YAG laser and tapping the residual 1.06 µm, 532 nm wavelength outputs for aerosol elastic scatter not only results in a compact lidar system but provides other additional benefits (as noted below).

Wavelengths greater than 1.5 µm have been used in other lidars (e.g., LR and SR BSDS) to render the lidar systems eye-safe. However, the 1.5 µm laser is a complex system requiring the 1.06 µm Nd:YAG output to be down shifted in an optical parametric oscillator OPO. Also, commonly available 1.5 µm detectors are not sufficiently sensitive; hence special detectors are needed, adding to the cost and complexity of the sensing systems. On the other hand, since the laser energy required for the PDL of the present invention can be small, the laser beams at both 532 nm and 1.06 µm can be made eye-safe by expanding the transmitted laser beam. The expansion of the transmitted laser beam is achieved by utilizing a telescope as both a transmitter and a receiver. Internal analysis of the aerosol backscatter signals have shown that a 20 km range is achieved with such an eye-safe lidar with a minimal averaging time of less than 0.5 sec, so that rapid scanning is feasible.

The particle sizes for naturally occurring aerosols range from 0.2-0.8 µm while the particle size for bio-aerosols range from 2-10 µm. Of the two chosen laser wavelengths, 532 nm is roughly equal to, and 1.06 µm is larger than, the natural aerosols, whereas the two chosen wavelengths are both smaller than the bio-aerosols. Hence, a differentiation between the naturally occurring aerosols and the bio-aerosols is possible by comparing the scattered signals at these two wavelengths. According to the present invention, combining the scattering differences with a 355 nm excited bio-fluorescence which has the potential for discrimination between man-made and naturally occurring bacteria provides an early and confirmatory warning system for the detection of a bio-aerosol presence.

Another embodiment of the portable digital lidar system of the present invention utilizes a common transmitter/receiver telescope system. Since the transmitter and receiver utilize a common optical conjugate point, both the transmitted beam and the receiver field-of-view stay aligned at all times, making the system immune to misalignment resulting from the displacement of telescope optics resulting from either vibration or thermal distortions. A single telescope which serves as both a transmitter and a receiver results in a compact, low-cost, and light system. Further, according to the present invention, internal scattering interferences can be minimized through the use of spatial and spectral filters.

For fluorescence measurement in the modular digital lidar system of the present invention, the UV laser pulse energy used is in a range about 500 µJ/pulse, assuming the laser pulse repetition rate to be 10 kHz, the output power is 5 W at 355 nm. The size and weight of the laser for generating this level of output is fairly large and utilizes appropriate thermal management and cooling for operation. Accordingly, in the present invention, it is preferable to dispose the laser source in a separate module removed from the lidar transmitter/receiver unit, as shown in FIG. 4A. Such a configuration brings several benefits such as: reducing the weight and size of lidar transmitter/receiver module, reducing the heat load on the transmitter/receiver module from the laser source, convenience in transportation, (i.e., easy to mount on vehicles), and ease of maintenance and field replacement.

To achieve this modularity, the UV laser output is divergently coupled to a fused silica fiber, which is then connected to the lidar transmitter (see FIG. 4A). For coupling the laser output into the fused silica fiber, techniques such as described in above-noted U.S. patent application Ser. No. 10/146,920. For example, a short focal length fused silica lens focuses the beam onto the fiber. For example, the high power, high energy, $TEM_{00}$ mode output beam can be focused into a small diameter (e.g. 350 to 500 µm core diameter) using the short focal length fused silica lens. The focal point occurs outside the fused silica fiber (i.e., divergently coupled), permitting damage free coupling of high power UV radiation and ensuring continuous operation for several 1000 s of hours.

Figure 6A:
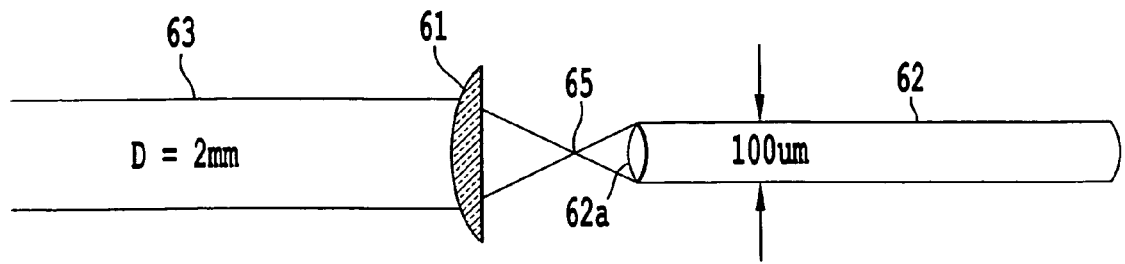
FIGS. 6A-6C are schematic diagrams illustrating various optical coupling mechanisms suitable for the present invention.

FIG. 6A is an exemplary schematic of a fiber optic coupling, according to the present invention, that does not require conventional convergent-coupling, thus maintaining a peak power density level below the surface or bulk damage threshold of the fiber optic. In the divergent-coupling configuration shown in FIG. 6A, a laser beam 63 is incident on a focusing lens 61 and focused to a focal point 65 in front of a fiber input surface 62a of a fiber 62. An aperture defined by the diameter of the fiber input surface 62a is matched to the fiber 62 at an expanding region of the laser beam after the laser beam focal point 65. In this coupling configuration, the maximum peak power density of the laser beam entering the fiber 62 is defined by the aperture size of the fiber (e.g. 100 µm) rather than the diffraction-limited focal spot size (e.g. 1 µm). For example, the peak power density of the above mentioned laser matched, according to the present invention, at the fiber diameter of 100 µm aperture is 3.3 MW/cm$^2$, as compared to the peak power density of 26 GW/cm$^2$ for the convergent-coupling. The peak power density of 3.3 MW/cm$^2$ is well below the surface or bulk damage threshold of optical fibers. Thus, the laser pulse which would normally exceed the damage threshold of the optical fiber in a tight-focusing coupling configuration can be safely coupled to the optical fiber without incurring damage.

Figure 6B:
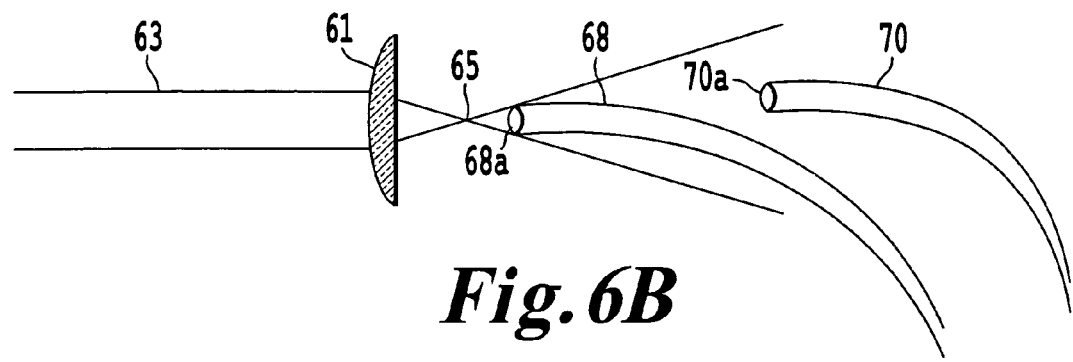

As such, in one embodiment of the present invention, a coupling mechanism (i.e., an optical coupling device) connects the fiber optic between the laser source and the transmitter. The optical coupling device can include a focusing lens to couple the laser pulses into the fiber optic. FIG. 6B depicts one optical coupling device that can be used in the present invention, and shows a fiber optic coupling in which a fiber is translated to vary the coupling efficiency. As shown in FIG. 6B, a laser beam 63 can be focused by focusing lens 61 onto a focal point 65 which is in front of the end surface 68a of the optical fiber 68. As a result, the end surface 68a of optical fiber 68 and the end surface 70a of the optical fiber 70 subtend portions of the expanding laser beam, and thus are not subjected to a power density exceeding the critical damage threshold. As seen in FIG. 6B, the coupling efficiency at the fiber position of 70a is much smaller than that of the fiber position 68a.

Figure 6C:
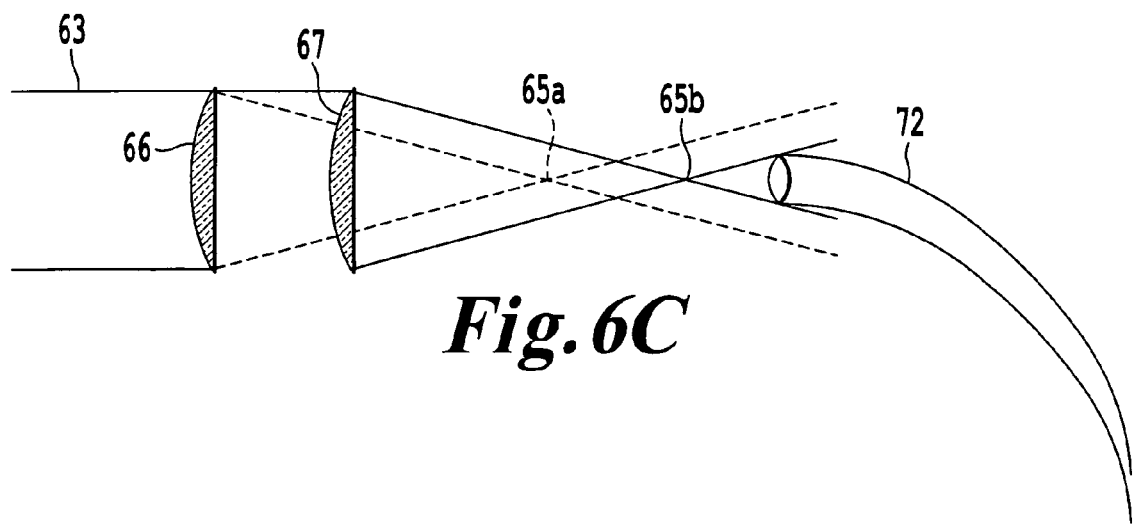

In one embodiment of the present invention, a position-setting device can translate the focusing lens or translate an entrance of the fiber optic along an optical axis between the focusing lens and the entrance to the fiber optic. As such, the position setting device sets a distance between the focusing lens and the entrance to the fiber optic such that the entrance is, for example, at a position beyond a focal point of the focusing lens where the laser pulse is divergent-coupled to the fiber optic. FIG. 6C is an exemplary schematic of an optical coupling that can be used in the present invention in which a lens is translated to vary the coupling efficiency. As shown in FIG. 6C, a laser beam 63 can be focused by a lens either at 65a or 65b position effectively varying the coupling efficiency of the fiber located at a fixed position.

Other techniques described in the above noted U.S. patent application Ser. No. 10/146,920 now published as U.S. Pat. Application Publication No. US 2003/0215181 A1 are also applicable in the present invention.

Figure 7:
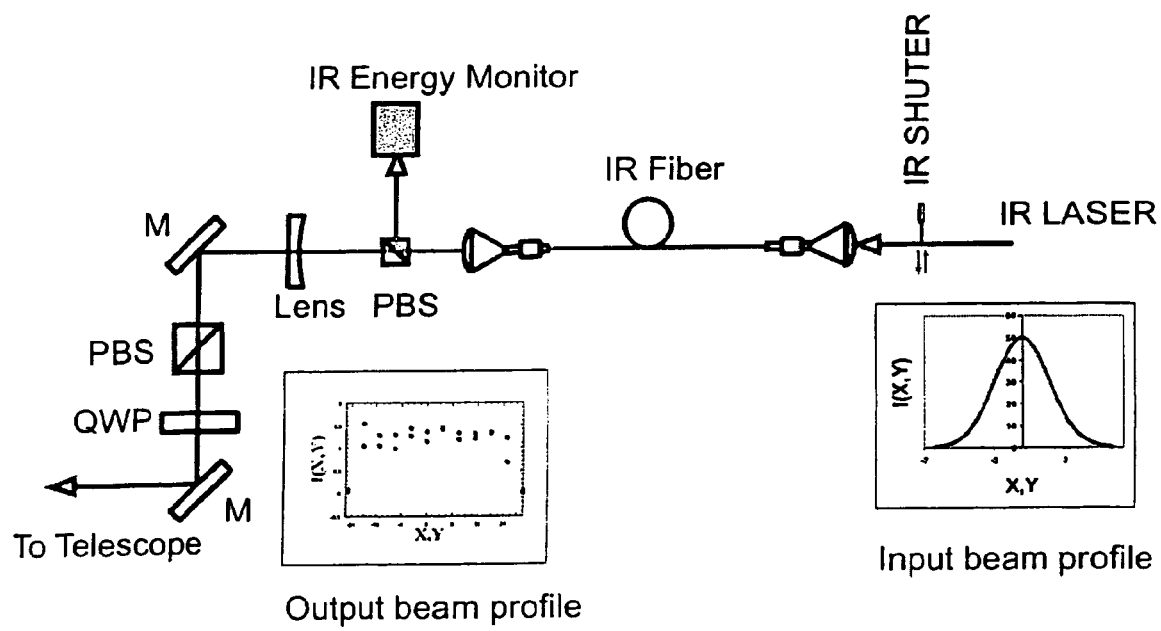
FIG. 7 is an optical schematic of a component layout for the lidar system according to an embodiment of the present invention utilizing a cone filter and an optical fiber to conform a Gaussian input beam.

Further, according to one embodiment of the present invention, the beam intensity at the input to the optical fiber (i.e., coming from the TEM$_{00}$ UV laser output) is Gaussian in shape, as shown in FIG. 7. The length of fiber can be chosen so as to ensure the intensity is uniform (top hat profile) at the exit from the fiber. This makes the lidar transmitted beam uniform in intensity and can be rendered eye-safe easier than a Gaussian beam whose peak intensity is much larger. Thus the top hat profile allows nearly three times more energy to be transmitter for the same Maximum Permissible Energy (MPE for human eye), than a Gaussian beam, whose peak energy density reaches the MPE even though the average energy density is lower than the MPE.

According to the present invention, this same technique is applicable for the near-IR laser also. By fiber coupling the output of the near-IR laser and by choosing a proper fiber size and length, the near-IR beam can also be made to be uniform. Thus, the transmitted energy from the lidar can be increased by a factor of three or more over that of a Gaussian beam, while still being eye-safe.

One alternative technique according to the present invention is to employ a cone lens for rendering the Gaussian beam profile to a uniform top-hat beam profile, as shown in FIG. 7. FIG. 7 depicts an optical schematic showing beam spreading. The transverse intensity distribution of input laser beam is Gaussian (TEM$_{00}$). Hence, the transmitted beam has a high energy density at the beam center where it may become eye hazard even when the total beam energy is below eye safe limit. This situation is corrected by using a fiber in the path that can change the Gaussian distribution to a top hat profile thus eliminating the hot spot in beam center. Either a multi-mode or a Polarization Maintaining (PM) fiber can be used. Since the IR beam is required to be polarized the multimode fiber where the polarization is randomized will provide a 50% loss because the output needs to be polarized again. Thus the PM fiber is preferable because of nearly loss free transformation.

According to the present invention, fiber coupling can permit the laser source to be a high power pulsed near-IR semiconductor laser diodes detached from the lidar transmitter/receiver. Utilization of high power pulsed near-IR semiconductor laser diodes permit the present invention to be more robust, more compact, and less expensive as compared to utilization of the diode-pumped solid state lasers. Furthermore, fiber coupling permits shorter wavelength near-IR semiconductor or solid state laser sources in the 850 to 1000 nm range to be utilized. For this wavelength of radiation, the silicon photo-detector quantum efficiency is nearly 5 to 6 times larger than at the 1047 nm wavelength corresponding to for example a Nd:YLF laser. As such, detection sensitivity is increased for the lidar backscattered signals.

Since the output from the multi-mode optical fiber is unpolarized even when the input beam may be polarized, in the present invention, a fiber output beam is rendered linearly polarized by employing a polarizer such as for example either a thin film polarizer or a prism polarizer at the output of the optical fiber. Furthermore, utilization of a polarizer in conjunction with a beam dump for rejecting the unused orthogonally polarized beam, produces a suitably polarized uniform intensity beam for use in the digital lidar system.

As noted above, for fluorescence measurements in the present invention, the UV laser pulse energy used is about 500 µJ/pulse. At this pulse energy level, internal scattering from the transmitter optical components can be large. Internal scattering has several undesirable effects such as for example causing the photodetector to saturate or overload the detector. In addition to the internal scatter, light scattered back to the receiver by atmospheric aerosols is also very strong for the first 100 meters or so which also can saturate the detector. If the detector is saturated, measurements are prevented until the detector comes out of saturation, which may occur at several microseconds (i.e., 100 s of meters of range) after the start of the pulse. A further consequence of the large signal incident on the photodetector is the generation of a signal induced after-pulse which adds a bias to the actual signal and increases the noise and thus degrades the lidar performance. Accordingly, the present invention reduces and/or eliminates the effects of internal and near-field scattering.

In one embodiment of the present invention, a second smaller aperture receiver is attached to the main scanner. The second receiver can be a simple lens (e.g., 10 cm dia, 20 cm focal length) or can be a catadioptric telescope such as for example the above-noted Cassegrainian configuration or a Maksutov configuration. The lens or telescope can couple light into the fiber optic cable which in turn is connected to a pin hole, wavelength selective filters, and a photodetector. The second receiver can collect backscattered light from a near distance $R_1$ to infinity. According to the present invention, the nearest distance $R_1$ can be adjusted for example to about 100 m to suit the application. Such implementation of a second smaller aperture receiver avoids the problems due to large internal scatter and near-field aerosol scattering. Further, the optical fiber attached to the receiver which controls the field of view of the second receiver can have a large field of view, for example, 0.5 or 1 mrad, making receiver alignment easier and simpler to maintain in field conditions.

Figure 8:
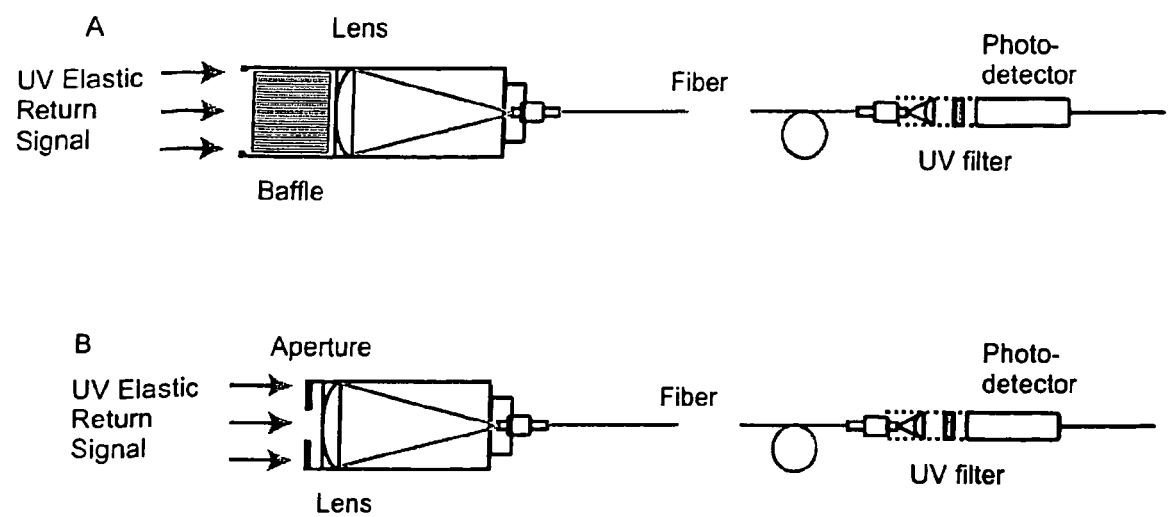
FIG. 8 is an optical schematic depicting component layouts for the lidar system according to an embodiment of the present invention utilized to detect an ultraviolet elastic return signal.

Another embodiment of the present invention includes an UV elastic second receiver, as shown in FIG. 8. FIG. 8 is an optical layout schematic of an UV elastic second receiver. The UV elastic second receiver can include a simple refractive telescope and a fiber coupled detector. A narrow bandpass filter permits only the elastic scattering to be measured while blocking the light in all the other wavelengths. The photodetector can be a photon counting PMT module. A baffle can be used to reduce the near field scattered light at large incident angles. The baffle can be attached in front of the receiver aperture to cut-off the strong near field scattering, as shown in FIG. 8. Baffles suitable for the present invention can be an assembly of long small diameter tubes stacked next to each other and assembled inside a lens hood strewed to the front of the receiver lens or telescope. These tubes limit the field of view of light (for example, a 100 mm long, 1 mm tube has a FOV of 5 mrad) coming into the receiver, which reach the detector due to multiple scattering in the optical components of the receiver.

In another embodiment of the present invention, the digital lidar geometry of collecting the received signal utilizes a large aperture telescope. But to switch out the strong scattered atmospheric signal, for a short period (for about 1 or 2 μs), the received signal is switched into a beam dump, preventing the detectors from saturating or suffering from overload. In this embodiment, the received signal is redirected after the first 1 or 2 μs into the photo-detector. Rather than using a beam dump, the present invention in one embodiment can utilize an acousto-optic beam deflector in line with the received signals and in front of the detectors, as shown for example in FIG. 4B. The extinction of an acousto-optic deflector is only about 80 to 90%. Hence, an in-line blocking switch still has 10 to 20% transmission enabling the detection of the backscattered signal throughout the strong scattering period. Further, the speed of the switch (I.e., the acousto-optic deflector) need not be very high because the pulse can be gradually deflected into the detector. Beam deflectors and/or switches in the present invention can be the above noted acoustic-optic beam deflectors, as well as electro-optic deflectors, mechanical mirror deflectors, membrane deforming mirrors, MEMS devices and saturable dye switches. The mechanical mirror deflectors and the membrane deforming mirrors can have electrostrictive and/or magentostrictive actuators. The acoustic-optic beam deflector can include an acousto-optic grating.

Figure 9:
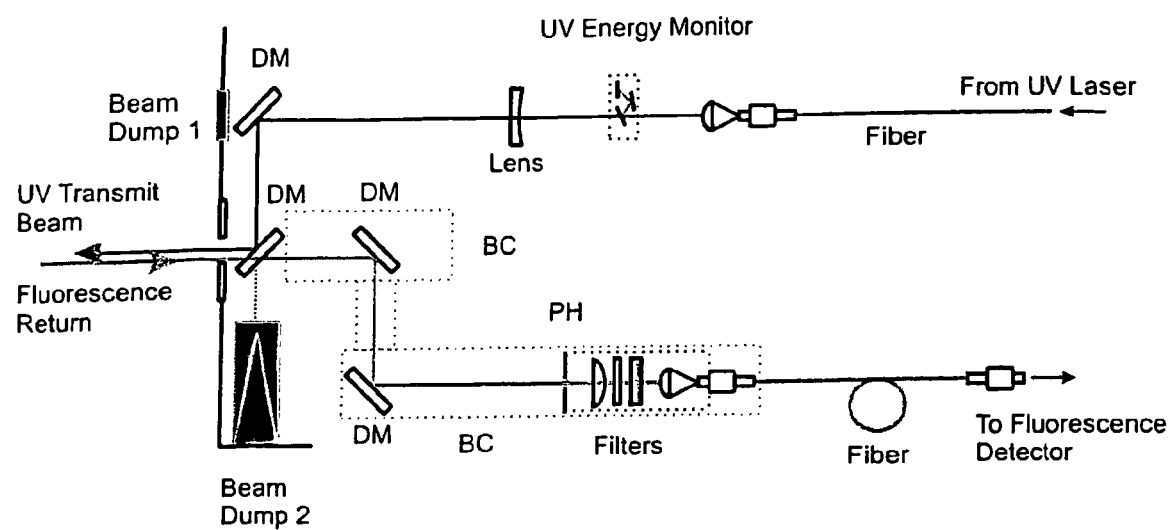
FIG. 9 is an optical schematic of a component layout for the lidar system according to an embodiment of the present invention showing a UV beam monitor.

FIG. 9 is an optical layout schematic of the UV laser transmitter section and the Fluorescence receiver channel. Gold plated beam dumps can be used to trap the unused UV beams. Since gold does not fluoresce, this ensures that no parasitic fluorescence is generated inside the lidar and reach the fluorescence detector. Other kinds of beam-deflectors or switches known in the art are suitable for use in the present invention. These include electro-optic deflectors, such as Pockel's devices in conjunction with a polarizer to cause extinction of the beam. Mechanical high speed low mass mirror deflectors employing electrostrictive or magentostrictive actuators, membrane deforming mirrors attached magnetostrictive or electrostrictive actuators, MEMS devices and/or saturable dye switches are suitable for use in the present invention. Use of beam-deflectors or switches extends the efficiency or range of the modular portable lidar system of the present invention.

Further, auto-fluorescence from many materials used in the lidar transmitter can contribute to a strong initial pulse as well as background signal to the fluorescence channel. To suppress auto-fluorescence, special procedures to clean the components effectively and the use of high purity optical components permit reductions in auto-fluorescence. However, substantial auto-fluorescence from other components remains. The present invention suppresses the auto fluorescence by using gold foil as a beam dump for UV light originating from the optical components. Since as noted above, gold does not fluoresce, a gold foil or film can be used as a cover on the exposed components in the path of UV beam.

In one embodiment of the present invention as shown in FIG. 9, the received signals (i.e. the received backscattered and received fluorescence signals) are separated into individual receiver channels and routed through separate optical fibers to separate detectors. Such an optical fiber based systems allow for easy maintenance, field replacement of parts, high immunity from stray light and effective separation of wavelength channels. High efficiency and high throughput can be obtained by matching the etendues of the different optical elements and the fibers.

For obtaining the high optical efficiency and throughput, the present invention utilizes in the trasmitter/reciever the above-noted Cassegrain telescope architecture which includes a combination of elliptical and spherical mirrors. By manufacturing the telescope for example from diamond turned aluminum mirrors, a robust fieldable telescope is obtained. High throughput is obtained by ensuring the image size is small and well within the acceptance of the receiver optical fibers.

In one embodiment of the present invention, the lidar system of the present invention autonomously conducts a surveillance over a large atmospheric volume by repeatedly scanning in the azimuth direction. Since the field of view of the lidar is small, the region that is covered is limited. For example, a 0.25 mrad FOV translates to a beam footprint of 2.5 m at 5 km range. To increase the coverage in the vertical direction, the modular lidar system of the present invention can add a small periodic dither to the scanner in the vertical direction. The dither, according to the present invention, effectively increases the scan coverage. The dither is provided by dither mechanism such as for example a reciprocator added between the transmitter/receiver and the frame to oscillate the telescope about the vertical direction.

The lidar system of the present invention is well-suited for biological standoff detection. The sensors utilized in the present invention addresses the requirements of high sensitivity and autonomous operation capability, eye-safety, and the ability to operate during the day for long-range detection.

Importantly, these attributes can be complemented with small size, rugged packaging, low power and maintenance requirements, and low cost. Further, the lidar system of the present invention can provide several enhancements for the aerosol and fluorescence portable digital lidar (PDL) for stand-off detection and discrimination of biological and chemical-warfare agents, which make it more versatile and suitable for civilian and military deployment either as a fixed ground based system or for mobile applications on several kinds of vehicles. The PDL can as noted utilize digital detection to achieve high sensitivity and excellent range capability in a very compact and light sensor package.

Enhancements in performance provide by the present invention can include, but are not limited to: 1) a fiber optic coupling scheme that makes the system modular and allows easy setup, operation and maintenance, 2) the incorporation of more than one kind of laser source to increase the operational efficiency and versatility, 3) methods for homogenizing beam intensity across the transmitter aperture to make the transmitted beam totally eye-safe, 4) the use of multiple receiver systems for increased performance by reducing detector overload and signal induced noise, 5) modification of field of view to increase alignment tolerance, 6) optical switching and other techniques to reduce signal induced noise, 7) inclusion of multiple wavelength fluorescence channels for increased discrimination, and 8) methods and procedures for autonomous detecting, tracking, and discriminating aerosol clouds.

Figure 10:
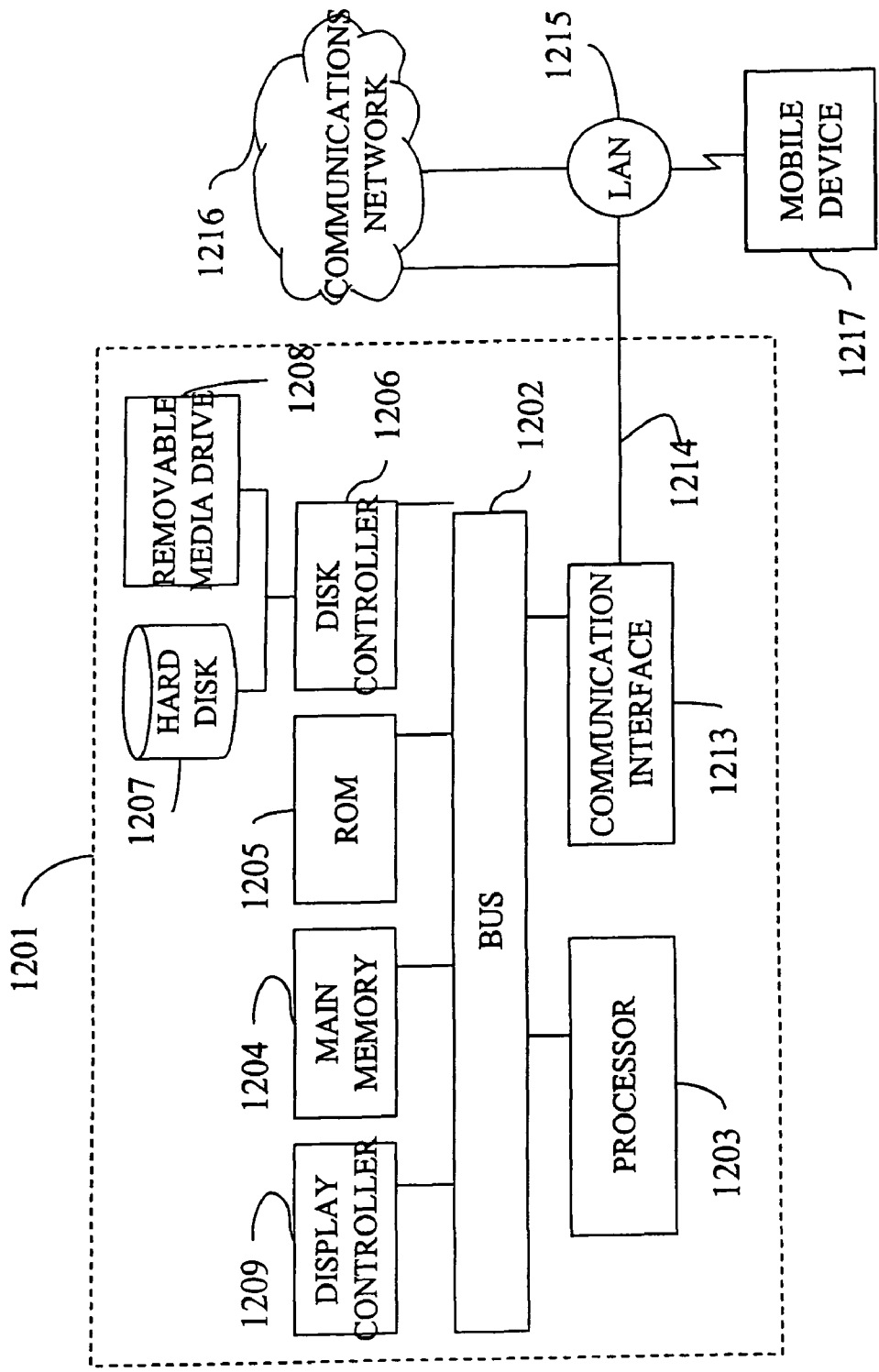
FIG. 10 is a diagram illustrating a computer system for implementing various embodiments of the present invention.

FIG. 10 illustrates one embodiment of a computer system 1201 in which the data acquisition and analysis system 50 of the present invention can be implemented. The computer system 1201 can be programmed and/or configured to perform any or all of the functions described above. The computer system 1201 can include a bus 1202 or other communication mechanism for communicating information, and a internal processor 1203 coupled with the bus 1202 for processing the information. The computer system 1201 includes a memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by the internal processor 1203. In addition, the memory 1204 may be used for storing temporary variables or other intermediate information during the execution of instructions by the internal processor 1203. The computer system 1201 preferably includes a non-volatile memory such as for example a read only memory (ROM) 1205 or other static storage device (e.g., programmable ROM (PROM), erasable PROM (EPROM), and electrically erasable PROM (EEPROM)) coupled to the bus 1202 for storing static information and instructions for the internal processor 1203.

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)). The computer system may also include one or more digital signal processors (DSPs) such as the TMS320 series of chips from Texas Instruments, the DSP56000, DSP56100, DSP56300, DSP56600, and DSP96000 series of chips from Motorola, the DSP1600 and DSP3200 series from Lucent Technologies or the ADSP2100 and ADSP21000 series from Analog Devices. Other processors especially designed to process analog signals that have been converted to the digital domain may also be used.

The computer system 1201 performs a portion or all of the processing steps of the invention in response to the internal processor 1203 executing one or more sequences of one or more instructions contained in a memory, such as the main memory 1204. Such instructions may be read into the main memory 1204 from another computer readable medium, such as a hard disk 1207 or a removable media drive 1208. Such instructions may be read into or from the main memory 1204 from another computer readable medium, such as from USB flash drives or jump drives. Such drives are sold-state memory devices which can act as floppy disks or hard drives under most computer operating systems. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media suitable for the present invention are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read. Such memory can include the above-noted jump drives.

Stored on any one or on a combination of computer readable media, the present invention includes software for controlling the computer system 1201, for driving a device or devices for implementing the invention, and for enabling the computer system 1201 to interact with a human user (e.g., to interact with consumable part disposal personnel). Such software may include, but is not limited to, device drivers, operating systems, development tools, and applications software. Such computer readable media further includes the computer program product of the present invention for performing all or a portion (if processing is distributed) of the processing performed in implementing the present invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the internal processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to internal processor 1203 for execution. For example, the instructions may initially be carried on a disk to a remote computer. The computer such as for example the process controller 120 can load the instructions for implementing all or a portion of the present invention remotely into a dynamic memory and send the instructions to the processing tool 110. An infrared detector coupled to the bus 1202 can receive the data carried in the infrared signal and place the data on the bus 1202. The bus 1202 carries the data to the main memory 1204, from which the internal processor 1203 retrieves and executes the instructions. The instructions received by the main memory 1204 may optionally be stored on storage device 1207 or 1208 either before or after execution by the internal processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213. Moreover, the network link 1214 may provide a connection through a LAN 1215 to a mobile device 1217 such as a personal digital assistant (PDA) laptop computer, or cellular telephone.

Numerous modifications and variations of the present invention are possible in light of the above teachings. It is therefore to be understood that within the scope of the appended claims, the present invention may be practiced otherwise than as specifically described herein.

The invention claimed is:

1. A system for detecting airborne agents, comprising:
 a laser source configured to provide laser pulses of at least two wavelengths;
 a transmitter configured to transmit the laser pulses;
 a coupling mechanism configured to remotely couple the laser pulses between the laser source and the transmitter, said coupling mechanism comprising 1) a fiber optic connected between the laser source and the transmitter and 2) at least one focusing lens configured to divergently couple said laser pulses into the fiber optic;
 a receiver configured to receive elastically backscattered signals and fluorescence signals from the airborne agents;
 a common telescope configured to focus a laser beam transmission of the laser pulses from the transmitter to a far field and to receive the elastically backscattered signals and the fluorescence signals from the far field; and
 a detection system comprising at least one of a backscatter optical detector configured to detect said elastically backscattered signals and a fluorescence optical detector configured to detect the fluorescence signals from the airborne agents.

2. The system of claim 1, wherein the receiver has a focal point located at a conjugate point of a focal point of the transmitter across from a beam splitter.

3. The system of claim 1, further comprising:
 a frame mounting optical components of the transmitter, the receiver, and the telescope.

4. The system of claim 3, wherein the frame is configured to maintain at least one predesignated direction of the laser beam transmission.

5. The system of claim 3, wherein the frame comprises:
 a dither mechanism configured to oscillate the telescope in a vertical scan direction during an azimuthal scan.

6. The system of claim 1, wherein the laser pulses comprises at least one of a 1.05 micron wavelength pulse in a range from 1.02 to 1.08 micron, a 525 nm wavelength pulse in a range from 510 to 540 micron, and a 350 nm wavelength pulse in a range from 340 nm to 360 nm.

7. The system of claim 6, wherein the laser is configured to pulse with an energy of at least 1 mJ at the 350 nm wavelength pulse and to pulse with an energy of at least a hundred µJ at the 1.05 micron wavelength pulse and the 525 nm wavelength pulse.

8. The system of claim 1, wherein the laser source is configured to pulse with a repetition rate of 1 kHz-10 kHz.

9. The system of claim 1, wherein the transmitter is configured to transmit the laser pulses coaxially and to expand the laser pulses with the common telescope such that the laser beam transmission is eye-safe.

10. The system of claim 1, wherein the receiver comprises:
 an optical separator configured to separate the elastically backscattered signals and the fluorescence signal.

11. The system of claim 10, wherein the optical separator comprises:
 optical fibers connected separately to the backscatter optical detector and the fluorescence optical detector; and
 the optical separator is configured to direct the elastically backscattered signals and the fluorescence signal into respective of the backscatter and fluorescence signal detectors via the optical fibers.

12. The system of claim 10, wherein the beam splitter comprises:

dichroic beam splitters configured to split the elastically backscattered signals and the fluorescence signal.

13. The system of claim 1, wherein the transmitter transmits a laser pulse in a 340 to 360 nm wavelength region configured to induce a fluorescence signal in a 440 nm wavelength region.

14. The system of claim 1, wherein the transmitter, the receiver, and the telescope are configured to suppress light interference from internally scattered laser light.

15. The system of claim 1, wherein the receiver comprises:
a field of view aperture located at the focal point of the receiver and configured to maximize a long-range return signal of 10-30 km.

16. The system of claim 15, wherein the field of view aperture comprises a variable size aperture.

17. The system of claim 15, wherein the aperture is located at a predetermined distance from sources of internal scatter in the receiver and configured to reduce an amount of internally scattered light detected by at least one of the backscatter and fluorescence signal detectors.

18. The system of claim 15, wherein the receiver comprises:
an optical baffle located between the receiver and at least one of the backscatter optical detector and the fluorescence optical detector.

19. The system of claim 18, wherein the optical baffle is attached in front of the receiver and is configured to cut off near field scattering.

20. The system of claim 19, wherein the optical baffle comprises:
a stack of adjacent tubes having a field of view from 2-10 mrad.

21. The system of claim 1, further comprising:
a polarizing beam splitter configured to separate the elastically backscattered signals and the fluorescence signal.

22. The system of claim 1, wherein the receiver comprises:
a rejection filter including a dichroic beam splitter, located in front of at least one of the backscatter optical detector and the fluorescence optical detector.

23. The system of claim 1, wherein optical components of the transmitter, the receiver, and the telescope comprise UV optical components configured to minimize extraneous fluorescence from the optical components.

24. The system of claim 23, wherein said optical components are covered with a gold foil to minimize said extraneous fluorescence.

25. The system of claim 1, further comprising:
an optical switch in front of the receiver configured to deflect backscattered UV light from the atmosphere; and
a gold beam dump to receive and absorb the deflected UV light.

26. The system of claim 1, wherein at least one of the backscatter optical detector and the fluorescence optical detector includes at least one of a beam deflector and an optical switch to temporarily filter the elastically backscattered signals and the fluorescence signal.

27. The system of claim 26, wherein the at least one of a beam deflector and an optical switch is disposed in front of the receiver, and comprises a synchronized gating to discriminate internal scattering light noise in the receiver from a return signal from the atmosphere to the receiver.

28. The system of claim 26, wherein said at least one of the beam deflector and the optical switch comprises at least one of an acoustic-optic beam deflector, an electro-optic deflector, mechanical mirror deflectors, membrane deforming mirrors, MEMS devices and saturable dye switches.

29. The system of claim 28, wherein the mechanical mirror deflectors and the membrane deforming mirrors include at least one of electrostrictive and magentostrictive actuators.

30. The system of Claim 28, wherein the acoustic-optic beam deflector includes an acousto-optic grating.

31. The system of claim 26, wherein said optical switch is configured to polarize the backscattered signals.

32. The system of claim 31, wherein said optical switch includes a Pockell cell.

33. The system of claim 1, wherein at least one of the backscatter optical detector and the fluorescence optical detector comprises a digital detector the output and includes an avalanche photodiode detector.

34. The system of claim 1, wherein at least one of the backscatter optical detector and the fluorescence optical detector comprises at least one of a solid state Geiger mode and an avalanche photodiode detector.

35. The system of claim 1, further comprising:
at least one optical fiber matched by aperture size and configured to couple a signal from a focal point of the receiver to at least one of the backscatter optical detector and the fluorescence optical detector.

36. The system of claim 35, wherein the at least one optical fiber and the at least one of the backscatter optical detector and the fluorescence optical detector are entendue matched.

37. The system of claim 1, wherein the laser source is configured to provide laser pulses of three wavelengths.

38. The system of claim 1, wherein the laser source comprises:
at least one of a Nd:YAG laser, a Nd:YLF laser, a Nd:YV04 laser, and a Yb:YAG laser.

39. The system of claim 1, wherein the laser source is configured to be tunable for differential lidar measurements of atmospheric trace gases.

40. The system of claim 1, wherein the digital detection system includes a Raman filter for Raman scattering measurements of specific atmospheric gases.

41. The system of claim 1, further comprising:
a computer configured to analyze the elastically backscattered signals to determine size distribution information.

42. The system of claim 41, wherein the computer is configured to analyze the fluorescence signal to determine an identity of the airborne agent.

43. The system of claim 41, wherein the computer is configured to identify objects in a field of view of the telescope.

44. The system of claim 43, wherein the objects identified comprise clouds of the airborne agents.

45. The system of claim 41, wherein the computer is configured to direct one-dimensional and two-dimensional analysis of received signals for object detection and discrimination.

46. The system of claim 45, wherein the one-dimensional analysis comprises evaluating noise at a distance from the telescope, comparing a fast response to a slow response, and identifying as objects received images having a discrepancy between the fast and slow response.

47. The system of claim 45, wherein the two-dimensional analysis comprises recognizing two-dimensional objects in view of the telescope by a connectivity of adjacent received waveforms and size-discriminating the objects.

48. The system of claim 41, wherein the computer is configured to analyze the fluorescence signal to determine if the airborne agent is a bio-warfare agent.

49. The system of claim 48, wherein the computer is configured to differentiate the bio-warfare agent by measuring multiple band fluorescence signals within a broad fluorescence band.

50. The system of claim 49, wherein the computer is configured to differentiate naturally occurring aerosols from the bio-warfare agent by analyzing the elastically backscattered signals from the laser pulses of two or more wavelengths.

51. The system of claim 49, wherein the computer is configured to differentiate naturally occurring aerosols from the bio-warfare agent by analyzing information on a time evolution of a size of an aerosol cloud and a settling rate of the aerosol cloud.

52. The system of claim 51, wherein the computer is configured to determine a wind speed and direction of the aerosol cloud by said size and said settling rate.

53. The system of claim 49, wherein the computer is configured to differentiate naturally occurring aerosols from the bio-warfare agent based on fluorescence signal data in conjunction wavelength backscattering data from laser pulses of at least three wavelengths.

54. The system of claim 53, wherein the computer is configured to differentiate naturally occurring aerosols from the bio-warfare agent by switching between a scanning mode to detect suspicious aerosol clouds at long-range and a non-scanning mode for high sensitivity fluorescence detection.

55. The system of claim 54, wherein the non-scanning mode is configured to utilize fluorescence measurements in a single fluorescent filter band to provide an indication of a presence of the bio-warfare agent in the suspicious aerosol clouds and utilizes multiple spectral bands for specific identification of the biological warfare agent or a class of biological warfare agents.

56. The system of claim 1, wherein the receiver comprises:
a catadioptric telescope having a combination of a spherical and elliptical reflecting surface.

57. The system of claim 1, wherein the receiver comprises:
an oversized field of view aperture configured to facilitate alignment of optical components in said system.

58. The system of claim 1, further comprising:
an anti-reflection window in front of the receiver.

59. A system for detecting airborne agents, comprising:
a laser source configured to provide laser pulses of at least two wavelengths;
a transmitter configured to transmit the laser pulses;
a coupling mechanism configured to remotely couple the laser pulses between the laser source and the transmitter;
a receiver configured to receive elastically backscattered signals and fluorescence signals from the airborne agents;
a common telescope configured to focus a laser beam transmission of the laser pulses from the transmitter to a far field and to receive the elastically backscattered signals and the fluorescence signals from the far field;
a detection system comprising at least one of a backscatter optical detector configured to detect said elastically backscattered signals and a fluorescence optical detector configured to detect the fluorescence signals from the airborne agents; and
a position-setting device configured to translate at least one of the focusing lens and an entrance of the fiber optic along an optical axis between the focusing lens and the entrance to the fiber optic, and configured to set a distance between the focusing lens and said entrance to the fiber optic such that said entrance is at a position beyond a focal point of the focusing lens where the laser pulse is divergent-coupled to the fiber optic.

60. The system of claim 59, wherein said optical coupling device is configured to couple a laser pulse with a non-Gausian-shaped beam profile into the fiber optic.

61. The system of claim 60, wherein said optical coupling device comprises a Cone lens.

62. The system of claim 61, wherein said optical coupling device comprises:
a polarizer disposed at an output end of the coupling mechanism prior to the transmitter.

63. The system of claim 62, wherein the polarizer comprises at least one a thin film polarizer and a prism polarizer.

64. The system of claim 62, wherein said optical coupling device is configured to transmit said laser pulse at an eye safe level of intensity.

65. A system for detecting airborne agents, comprising:
a laser source configured to provide laser pulses of at least two wavelengths;
a transmitter configured to transmit the laser pulses;
a coupling mechanism configured to remotely and divergently couple the laser pulses from the laser source to the transmitter;
a receiver configured to receive elastically backscattered signals and fluorescence signals from the airborne agents;
a common telescope configured to focus a laser beam transmission of the laser pulses from the transmitter to a far field and to receive the elastically backscattered signals and the fluorescence signals from the far field;
a detection system comprising at least one of a backscatter optical detector configured to detect said elastically backscattered signals and a fluorescence optical detector configured to detect the fluorescence signals from the airborne agents; and
an enclosure for at least the transmitter to provide an hermetic seal of optical components in the transmitter from atmospheric gases.

66. The system of claim 65, further comprising:
a desiccant to remove moisture from an interior of said enclosure.

67. A system for detecting and identifying airborne agents, comprising:
means for producing laser pulses;
means for transmitting the laser pulses of at least two wavelengths;
means for remote coupling the laser pulses between the means for producing and means for transmitting by way of a fiber optic between the means for producing and the means for transmitting and by way of means to divergently couple the laser pulses into the fiber optic;
means for receiving elastically backscattered signals from the airborne agents and fluorescence signals from the airborne agents;
means for detecting a presence of the airborne agents by analyzing differences in the elastically backscattered signals from the laser pulse of at least two wavelengths; and
means for identifying of the airborne agents by analyzing a fluorescence signal induced by transmitted laser pulses.

68. The system of claim 67, wherein said means for transmitting and said means for receiving comprise a common telescope.

69. The system of claim 67, further comprising:
means for aligning autonomously the system including said means for transmitting and said means for receiving.

70. The system of claim 67, further comprising:
means for positioning a receiver field of view aperture at a conjugate point of the means for transmitting to maximize a reception of the elastically backscattered signals and the fluorescence signals.

71. The system of claim 67, further comprising:
means for mounting transmitter and receiver optical components on a single board to withstand vibration and shocks encountered in field operations.
72. The system of claim 67, further comprising:
means for attaching said means for transmitting and said means for receiving to a frame, said means for attaching having a dither mechanism to oscillate the means for transmitting in a vertical scan direction.
73. The system of claim 67, wherein the means for producing laser pulses comprise:
means for pulsing a laser with at least one of a 1.05 micron wavelength pulse, a 525 nm wavelength pulse, and a 350 nm wavelength pulse.
74. The system of claim 73, wherein the means for pulsing comprise:
means for pulsing with an energy of at least 1 mJ at the 350 nm wavelength pulse and with an energy of at least a few hundred µJ at the 1.05 micron wavelength pulse and the 525 nm wavelength pulse.
75. The system of claim 73, wherein the means for pulsing comprise:
means for pulsing with a repetition rate of 1-10 kHz.
76. The system of claim 67, wherein the means for transmitting comprise:
means for transmitting the laser pulses coaxially; and means for expanding the laser pulses such that a laser beam transmission is eye-safe.
77. The system of claim 67, wherein the means for transmitting comprise:
means for transmitting a laser pulse in a 340 to 360 nm wavelength region to induce a fluorescence signal in a 440 nm wavelength region.
78. The system of claim 67, wherein the means for receiving comprise:
means for filtering temporarily the elastically backscattered signals and the fluorescence signal.
79. The system of claim 67, wherein the means for transmitting comprise:
means for transmitting tunable laser pulses suitable for differential lidar measurements of atmospheric trace gases.
80. The system of claim 67, wherein the means for receiving comprise:
means for filtering at least one of the elastically backscattered signals with a Raman filter to resolve a Raman scattering signal of a specific gas.
81. The system of claim 67, wherein the means for receiving comprise:
means for positioning a receiver field stop to maximize a long-range return signal of 10-30 km.
82. The system of claim 67, wherein the means for transmitting comprise:
means for directing the transmitted laser pulses in azimuthal and zenith directions.
83. The system of claim 67, further comprising:
means for analyzing the elastically backscattered signals to determine size distribution information.
84. The system of claim 67, further comprising:
means for analyzing the fluorescence signal to determine an identity of the airborne agent.
85. The system of claim 67, further comprising:
means for analyzing the fluorescence signal to determine if the airborne agent is a bio-warfare agent.
86. The system of claim 85, wherein the means for analyzing comprises:
means for differentiating the bio-warfare agent by measuring multiple band fluorescence signals within a broad fluorescence band.
87. The system of claim 86, wherein the means for differentiating comprise:
means for differentiating naturally occurring aerosols from the bio-warfare agent by analyzing the elastically backscattered signals from laser pulses of at least three wavelengths.
88. The system of claim 86, wherein the means for differentiating comprise:
means for differentiating naturally occurring aerosols from the bio-warfare agent by analyzing information on a time evolution of a size of an aerosol cloud and a settling rate of the aerosol cloud.
89. The system of claim 88, wherein the means for analyzing comprise:
means for determining a wind speed and direction of the aerosol cloud by said size and said settling rate.
90. The system of claim 86, wherein the means for differentiating comprise:
means for differentiating naturally occurring aerosols from the bio-warfare agent based on fluorescence signal data in conjunction wavelength backscattering data from laser pulses of at least three wavelengths.
91. The system of claim 86, wherein the means for differentiating comprise:
means for differentiating naturally occurring aerosols from the bio-warfare agent by switching between a scanning mode to detect suspicious aerosol clouds at long-range and a non-scanning mode for high sensitivity fluorescence detection.
92. The system of claim 86, wherein the means for differentiating comprise:
means for differentiating naturally occurring aerosols from the bio-warfare agent by utilizing fluorescence measurements in a single fluorescent band to provide a general indication of a presence of the bio-warfare agent in the suspicious aerosol cloud and utilizes multiple spectral bands for specific identification of the biological warfare agent or a class of biological warfare agents.
93. The system of claim 67, wherein the means for receiving comprise:
means for dumping backscattered UV light during a transient time after transmitting the laser pulse.
94. The system of claim 67, wherein the means for remote coupling divergently couples the laser pulse.
95. The system of claim 67, wherein the means for remote coupling spatially spreads the laser pulse to an eye safe level.

* * * * *